(12) United States Patent
Bihel et al.

(10) Patent No.: US 10,752,976 B2
(45) Date of Patent: Aug. 25, 2020

(54) PROCESS OF EXTRACTION OF A PLATINUM GROUP METAL OR GOLD FROM ORGANIC COMPOSITIONS WITH SURFACTANTS

(71) Applicants: Centre National de la Recherche Scientifique, Paris (FR); Universite d'Avignon et des Pays de Vaucluse, Avignon (FR); Universite de Strasbourg, Strasbourg (FR); Commissariat a l'Energie Atomique et aux Energies Alternatives, Paris (FR); Ecole Nationale Superieure de Chimie de Montpellier, Montpellier (FR); Universite de Montpellier, Montpellier (FR)

(72) Inventors: Frédéric Jean-Jacques Bihel, Fegersheim (FR); Damien Bourgeois, Aramon (FR); Stéphane Desgranges, Avignon (FR); Daniel Meyer, Saint Genies de Comolas (FR); Christiane Contino-Pepin, Althen des Paluds (FR); Martine Schmitt, Strasbourg (FR); Patrick Hervé Denis Wagner, Brumath (FR)

(73) Assignees: Universite de Strasbourg, Strasbourg (FR); Centre National de la Recherche Scientifique, Paris (FR); Avignon Universite, Avignon (FR); Comissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 16/302,818

(22) PCT Filed: May 19, 2017

(86) PCT No.: PCT/EP2017/062161
§ 371 (c)(1),
(2) Date: Nov. 19, 2018

(87) PCT Pub. No.: WO2017/198846
PCT Pub. Date: Nov. 23, 2017

(65) Prior Publication Data
US 2019/0316223 A1    Oct. 17, 2019

(30) Foreign Application Priority Data

May 19, 2016  (WO) .................. PCT/IB2016/052952
Jul. 21, 2016  (EP) .................................... 16180529

(51) Int. Cl.
*C22B 3/10* (2006.01)
*C08G 83/00* (2006.01)
(Continued)

(52) U.S. Cl.
CPC ................. *C22B 3/10* (2013.01); *B01J 23/56* (2013.01); *B01J 31/064* (2013.01); *C08F 2/30* (2013.01);
(Continued)

(58) Field of Classification Search
CPC ..................................................... C08G 83/03
See application file for complete search history.

(56) References Cited

FOREIGN PATENT DOCUMENTS

| WO | 92/02560 A1 | 2/1992 |
| WO | 2016/008932 A1 | 1/2016 |

OTHER PUBLICATIONS

Barthelemy et al., "A New Class of Sulfoxide Surfactants derived from Tris. Synthesis and Preliminary Assessments of their Properties," Bioorganic & Medicinal Chemistry Letters, 8: 1559-1562 (1998).

(Continued)

*Primary Examiner* — Melissa S Swain
(74) *Attorney, Agent, or Firm* — Morgan, Lewis & Bockius LLP

(57) ABSTRACT

The present invention is in the field of surfactants to extract a platinum group metal or gold, in particular palladium, from organic compositions. In particular, the invention concerns the use of surfactants to back-extract a platinum group metal or gold, in particular palladium, from organic compositions further comprising an extractant of said platinum group metal or gold, in particular palladium from an aqueous solution.

13 Claims, 1 Drawing Sheet

SDS    TPGS-750-M    DendriTAC H12G₀diTAC (5*2)

(51) Int. Cl.
| | |
|---|---|
| B01J 23/56 | (2006.01) |
| B01J 31/06 | (2006.01) |
| C08F 2/30 | (2006.01) |
| C22B 3/26 | (2006.01) |
| C22B 3/44 | (2006.01) |
| C22B 3/00 | (2006.01) |
| C22B 15/00 | (2006.01) |

(52) U.S. Cl.
CPC ......... *C08G 83/003* (2013.01); *C08G 83/008* (2013.01); *C22B 3/0097* (2013.01); *C22B 3/44* (2013.01); *C22B 11/044* (2013.01); *C22B 15/0084* (2013.01)

(56) References Cited

OTHER PUBLICATIONS

Polidori et al., "Synthesis and aggregation behaviour of symmetric glycosylated bolaamphiphiles in water," ARKIVOC, iv: 73-89 (2006).

Barthelemy et al., "Synthesis and Preliminary Assessments of Ethyl-Terminated Perfluoroalkyl Nonionic Surfactants Derived from Tris(hydroxymethyl)acrylamidomethane," Organic Letters, 1: 1689-1692 (1999).

Sigma-Aldrich, "Designer Surfactant-Enabled Cross-Couplings in Water at Room Temperature," 45 (2012).

International Search Report issued in corresponding International Patent Application No. PCT/EP2017/062161 dated Aug. 4, 2017.

Written Opinion issued in corresponding International Patent Application No. PCT/EP2017/062161 dated Aug. 4, 2017.

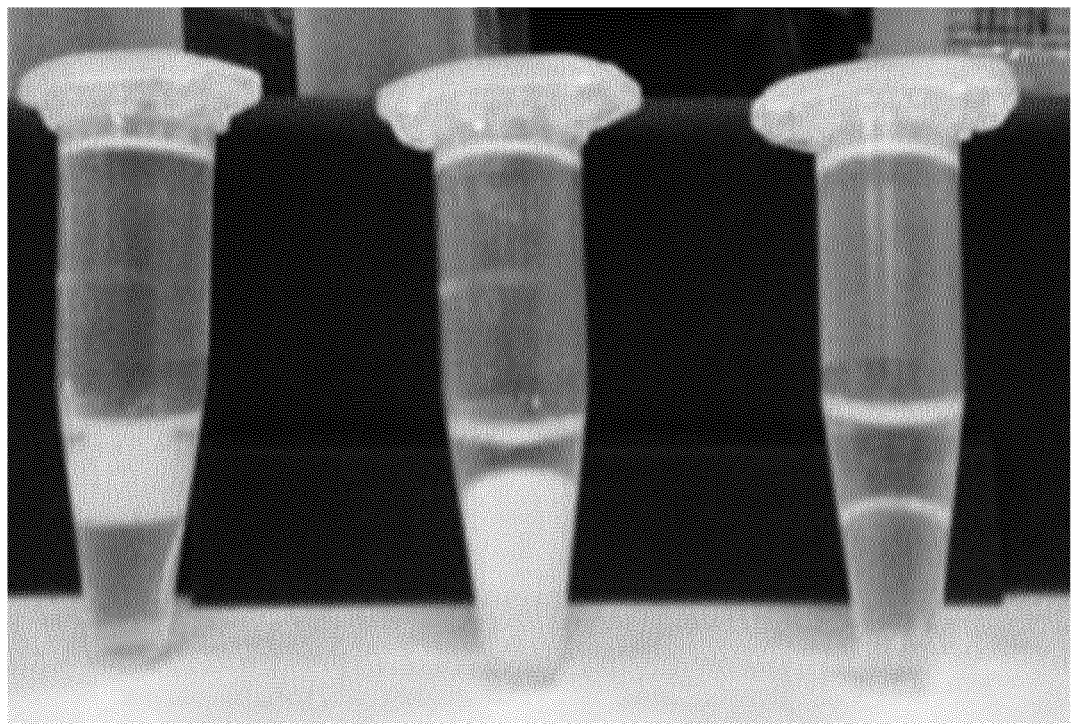
SDS            TPGS-750-M      DendriTAC $H12G_0diTAC$ (5*2)

PROCESS OF EXTRACTION OF A PLATINUM GROUP METAL OR GOLD FROM ORGANIC COMPOSITIONS WITH SURFACTANTS

The present invention is in the field of surfactants to extract a platinum group metal or gold, in particular palladium, from organic compositions. In particular, the invention concerns the use of surfactants to back-extract a platinum group metal or gold, in particular palladium, from organic compositions further comprising an extractant of said platinum group metal or gold, in particular palladium from an aqueous solution.

Palladium (Pd) is a semi-precious metal, the supply of which remains strategic due to the geographic location of deposits and therefore, to the production, which is limited to a few countries (mainly Russia and South Africa). Moreover, tensions exist on the palladium market, due to the end of the inventories held by Russia, which allowed the market to relax, as well as a steady increase in the demand for palladium. In fact, all the metals of the platinum group, including platinum (Pt), palladium and rhodium (Rh) are considered as strategic by the EU and the US, the production of these three metals being closely related.

Gold (Au) is a precious metal which is also strategic, due to its use for investments and in industry.

Platinum group metals and gold, in particular palladium, are metals having interesting catalytic properties, and a good resistance to corrosion.

Hence, platinum, palladium, rhodium and gold are in particular used in the manufacture of catalytic converters for the automotive. The evolution of the palladium demand is in fact largely linked to the growth of the automotive market.

Platinum group metal and gold are also used in the chemical industry, as catalysts.

It is estimated that about one quarter of the amount of palladium consumed annually originates from recycled wastes. This recycling relies exclusively on the recycling of catalytic converters, a homogeneous source of palladium, treated in hydrochloric acid medium. The development of new recycling processes is an upcoming area of economic interest.

The valuation of wastes of electrical and electronic equipment (WEEE) also referred to as "urban mine" is a booming thematic, and represents an important potential source of platinum group metals, in particular palladium, and gold.

Whatever its source (mine ore, recycling of converters or wastes, etc. . . . ), Pd is separated and refined thanks to classical hydrometallurgy techniques, and different technologies can be used, such as liquid-liquid extraction (or solvent extraction), electrochemistry, selective precipitation, supported liquid membranes or ion exchange resins.

In the case of palladium liquid-liquid extraction, many extractants have been developed and are very effective for selective extraction of the palladium from the acidic aqueous phase to an organic phase, such as malonamides, alkyl sulfides, sulfoxides produced by mono-sulfide oxidation, hydroxyoximes, amines or ammonium salts, phosphorus derivatives such as alkyl phosphine oxides and phosphine sulfides, ketones, thio and dithio-diglycolamides.

Palladium is generally back-extracted from the organic phase into an aqueous phase employing an aqueous solution of HCl or ammonia, then purified by two methods that can be summarized as follows:

Precipitation of palladium dichlorodiamine in two stages with solubilization of hexachloropalladate by ammonia to give [Pd(NH$_3$)$_4$]Cl$_2$, followed by precipitation in acidic conditions of palladium dichlorodiamine [PdCl$_2$(NH$_3$)$_2$]. The latter is redissolved with an aqueous ammonia solution to form the palladium dichlorotetramine [Pd(NH$_3$)$_4$]Cl$_2$ and precipitated again by acidification. Palladium dichlorotetramine may also be extracted by a dialkylsulfide and then re-extracted with an ammoniac solution. Very pure [PdCl$_2$(NH$_3$)$_2$] is obtained by precipitation at pH 1; or Solubilization of hexachloropalladium by N$_2$H$_4$ to give (NH$_4$)$_2$[PdCl$_4$]. (NH$_4$)$_2$[PdCl$_6$] may be obtained by Cl$_2$ gas treatment and addition of NH$_4$Cl.

However, these methods involve hazardous chemicals and imply purification extra steps. Hence, these methods of Pd back-extractions are neither environmentally friendly nor cost-effective.

In 2012, the Rio Declaration on Environment and Development has set the challenge to our worldwide society to reach a "sustainable development" through the implementation of innovative scientific, technologic and social tools. It is a real challenge for the chemical industry, as one of the most important goals of sustainable development consists in reducing the adverse consequences of the substances that we use and generate. Worldwide demand for environmentally friendly chemical processes requires novel and cost-effective approaches, which will be the pedestal of renewal of our chemical industry. This conceptual revolution is already underway with the growing development of the Green Chemistry.

One of the key area of Green Chemistry is the elimination of solvents in chemical processes or the replacement of hazardous solvents with environmental benign solvents. In 2009, the ACS Green Chemistry Institute (composed by 12 major pharmaceutical companies such as Pfizer, Novartis, and GSK) established that solvents contribute to more than 50% of materials used in manufacture of active pharmaceutical compounds, and consequently, the development of greener solvent alternatives should become a strategic priority for chemical industry. While the environmental implications are clear, there are also economic incentives to get organic solvents out of organic reactions. Up-front costs associated with their purchase, and then expenses earmarked for their proper disposal, are very significant in the global production costs of a chemical compound. Moreover, using organic solvents is also an issue in terms of toxicity and flammability, and has a clear impact on worker safety. Consequently, selecting alternative solvents that will have limited impact on health and environment has become a major issue for our community. Solvent-free alternative is, of course, the best solution, but most of the organic reactions require a solvent. Ionic liquids, supercritical media and other non-conventional media have been described as efficient alternatives to conventional organic solvents, but using water as alternative solvent appears to be a very attractive approach.

Although some chemical reactions were successfully developed in water, in general manner, the poor solubility of organic reagents and catalysts was described as a strong limitation to this approach. To circumvent the solubility issue, some surfactants were used in water to form hydrophobic nanoreactors. Indeed, thanks to their amphiphilic nature, surfactants in water undergo spontaneous self-assembly into micellar form. Each micelle represents a nanoreactor with a lipophilic core that will function as reaction vessel in which the organic transformation involving water-insoluble reagents can occur. Used above the critical micelle concentration (CMC, typically on the order of $10^{-3}$ to $10^{-4}$ M), very little of this surfactant will be required to generate micellar nanoreactors. The proof of concept of this micellar-approach was successfully proved by Bruce Lipshutz et al. (Aldrichimica Acta, 2008, 41, 59) for well-known palladium-catalyzed cross-coupling reactions such as the Suzuki-Miyaura, Heck, and Sonogashira reactions, using TPGS-750-M as surfactant (2 wt % in water). Interestingly, in most cases, the "hydrophobic effect" characteristic of aqueous micellar catalysis allows cross-coupling reactions to take place at room temperature, while heating would be required under traditional conditions. Indeed, as all the reagents are together in a small volume defined by the size of the micelle, this vicinity facilitates the occurrence of the reaction at lower temperature. Reactions under micellar conditions are generally very easy to proceed as everything can be done in air. Workup is also easy to handle, as when the reaction is complete, no additional water needs to be added. Only a limited amount of a single organic solvent (e.g. EtOAc) has to be used for extraction of organic remaining reactants and resulting products. As the surfactant remains in the aqueous phase in the reaction vessel, the system can be reused several times in many cases, despite the presence of water-soluble byproducts.

There is thus a need to back-extract the platinum group metals and/or gold, in particular Pd(II), contained in an organic phase, resulting in particular from liquid-liquid extraction, in order to obtain an aqueous phase containing surfactants and the platinum group metal and/or gold, in particular Pd(II), that may directly be used in platinum group metal or gold-catalyzed reactions, in particular palladium-catalyzed reactions, under micellar conditions.

However, the Inventors have found that this back extraction cannot be performed with surfactants classically used in micellar catalysis, such as TPGS-750-M, or versatile surfactants known in the art, such as SDS, Zonyl UR or Brij 35. Indeed, a very stable emulsion is obtained with these surfactants, instead of a clean separation of the organic and the aqueous phases.

Accordingly, it is an object of the present invention to provide surfactants enabling a clean separation of the organic and the aqueous phases after the extraction, in particular the back extraction, of the at least one metal chosen from the platinum group metals and gold, in particular palladium, from an organic phase into an aqueous micellar solution.

A further goal of the present invention is to obtain an aqueous phase wherein the platinum group metal or gold, in particular palladium, is stable enough, in particular towards hydrolysis, to perform directly aqueous-based platinum group metals or gold-catalyzed reactions, in particular palladium-catalyzed reactions.

Inventors have for the first time demonstrated that a selection of surfactants enables a clean separation of the organic and the aqueous phases after said extraction, in particular back extraction, and that said aqueous phase, which contains a platinum group metal or gold, in particular palladium, can directly be used, without further step, to perform aqueous-based platinum group metal or gold-catalyzed reactions, in particular palladium-catalyzed reactions.

Thus, in one aspect, the present invention relates to a process of extraction of at least one metal chosen from the platinum group metals and gold, in particular Pd(II), from a first organic liquid composition comprising:
   at least one metal chosen from the platinum group metals and gold, in particular Pd(II), and
   an organic solvent, said organic solvent being water immiscible, said process comprising the following steps:

a) contacting said first organic liquid composition with a first aqueous solution comprising a surfactant to obtain, after phase separation,
   a second aqueous solution comprising the at least one metal chosen from the platinum group metals and gold, in particular Pd(II), and the surfactant, and
   a second organic liquid composition comprising the organic solvent;

b) recovering of said second aqueous solution, said surfactant comprising:
   an hydrophobic central core of valence m equal to 1, 2 or 3;
   when m=1, a hydrophilic group G of the following formula, attached to the central core:

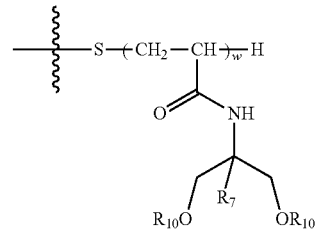

wherein:

$R_7$ is selected from H, $C_1$-$C_6$ alkyl and $CH_2OR_{10}$;

$R_{10}$ is H or a monosaccharide selected from glucose, galactose, mannose;

w is an integer from 1 to 30, preferably from 4 to 25;

when m=2 or 3, the surfactant being then a dendrimer of generation n, said surfactant comprising:

generation chains attached to the central core and branching around the core; and an hydrophilic terminal group at the end of each generation chain;

wherein n is an integer from 0 to 12;

the hydrophilic terminal group comprises:
   a mono-, oligo- or polysaccharide residue,
   a cyclodextrin residue,
   a polyethylene glycol (PEG) residue,
   a peptide residue,
   a tris(hydroxymethyl)aminoethane (Tris), or
   a 2-amino-2-methylpropane-1,3-diol;

the central core being:

when m=1, a-L'-W' group, wherein:

W' is $R_F$ or a group selected from $W'_1$, $W'_2$ or $W'_3$:

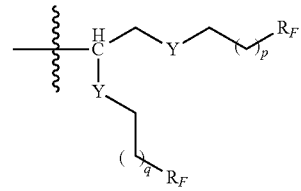

$W'_1$

-continued

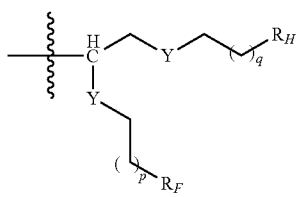
W'₂

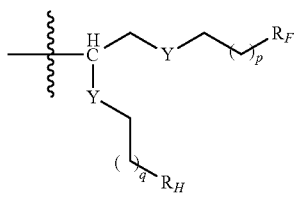
W'₃

$R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L' is a linear or branched $C_1$-$C_{12}$ alkylene group, optionally interrupted by one or more groups Y';

Y' at each occurrence is chosen from —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH—, —O— or —S—;

Y at each occurrence is chosen from —S—, —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH— or —O—;

when m=2 or 3, a group of formula (Ia) or (Ib):

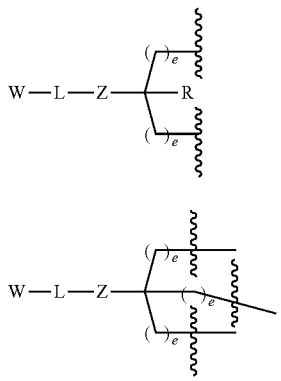

(Ia)

(Ib)

wherein:
W is $R_F$ or a group selected from $W_0$, $W_1$, $W_2$ or $W_3$:

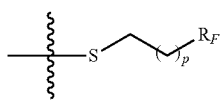
$W_0$

-continued

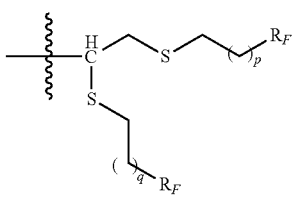
$W_1$

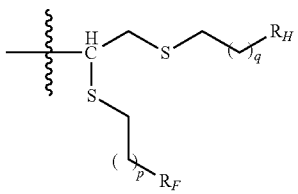
$W_2$

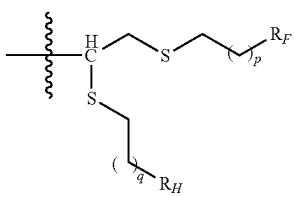
$W_3$ $R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L is a linear or branched $C_1$-$C_{12}$ alkylene group, optionally interrupted by one or more —O—, —S—,
Z is C(=O)NH or NHC(=O),
R is a $C_1$-$C_6$ alkyl group, and
e is at each occurrence independently selected from 0, 1, 2, 3 or 4.

Steps a) and b) can be performed thanks to the techniques well known from the one skilled in the art, in particular by using a mixer-settler, centrifuge extractor or pulsed column.

When m=1, the surfactant is as illustrated in the following scheme 1a:

Scheme 1a

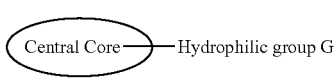

m = 1

As used herein, the "valence m of the central core" refers for m=2 and 3 to the number of generation chains attached to the central core, as illustrated in the following scheme 1b:

Scheme 1b

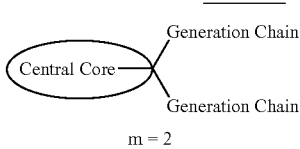

m = 2

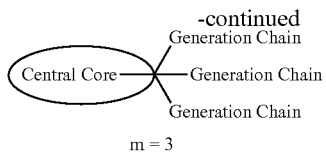

m = 3

As used herein, a dendrimer of generation n=0, means that the m generation chains are connected to the central core through a first branching point ($G_0$), corresponding to the valence of the central core. A dendrimer of generation n=1 means that each of the m generation chains ramifies itself once, more specifically at the branching point $G_1$ (see scheme 2).

Scheme 2

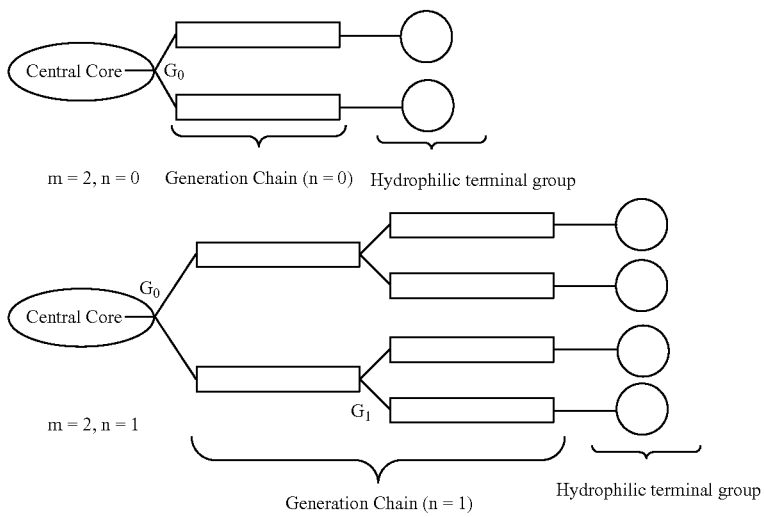

Each generation chain of the amphiphilic dendrimers according to the invention is ended by an hydrophilic terminal group.

In this respect, the mono-, oligo- or polysaccharide residue may be notably glucose, galactose, mannose, arabinose, ribose, maltose, lactose, hyaluronic acid.

The cyclodextrin residue may be selected from α, β or γ-Cyclodextrin.

The peptide residue may be chosen from linear or cyclic peptides containing the arginine-glycine-aspartic acid (RGD) sequence.

In a preferred embodiment, the first organic liquid composition results from the liquid/liquid extraction of an original acidic aqueous phase comprising at least one metal chosen from the platinum group metals and gold, in particular Pd(II), with said organic solvent.

In a particular embodiment, the organic solvent comprises or consists of an extractant of at least one metal chosen from the platinum group metals and gold, in particular Pd(II), from an acidic aqueous solution and optionally, an organic diluent and/or a phase modifier.

In a particular embodiment, the organic solvent comprises or consists of an extractant of at least one metal chosen from the platinum group metals and gold, in particular Pd(II), from an acidic aqueous solution.

In a another more particular embodiment, the organic solvent comprises or consists of an extractant of at least one metal chosen from the platinum group metals and gold, in particular Pd(II), from an acidic aqueous solution and an organic diluent.

In another more particular embodiment, the organic solvent comprises or consists of an extractant of at least one metal chosen from the platinum group metals and gold, in particular Pd(II), from an acidic aqueous solution, an organic diluent and a phase modifier.

In a preferred embodiment, the extractant is chosen from the group comprising malonamides, alkyl sulfides, sulfoxides, hydroxyoximes, amines, ammonium salts, alkyl phosphine oxides, phosphine sulfides, ketones, thio and dithio-diglycolamides, in particular malonamides, alkyl phosphine oxides and sulfoxides.

Malonamides as extractants, in particular dimethyldibutyltetradecylmalonamide, are described in WO2016008932.

Alkyl sulfides, for example dioctylsulfure (or DOS), dihexylsulfure (or DHS) and polysulfides, have also been described as extractants (Tatarchuk et al., Russ. J. Inorg. Chem. 2002, 47, 1917-1921; Russ. J. Inorg. Chem. 2009, 54, 1332-1338; Torgov et al., Russ. J. Inorg. Chem. 2013, 58, 1383-1389).

Sulfoxides produced by the mono-sulfide oxidation, in particular dioctylsulfoxyde (or DOSO; Rizvi et al., September Sci. Tech. 1996, 31, 1805-1816) and bis(2-ethylhexyl) sulfoxide (or BESO; Shukla Singh et al., Anal. Chim. Acta 1993, 276, 181-187) have been tested successfully as extractants.

Hydroxyoximes (Dakshinamoorthy et al. Desalination 2008, 232, 26-36), amines or ammonium salts (Mezhov et al., Radiochemistry, 2002, 44, 146-150), alkyl phosphine oxides (Gupta Singh, Hydrometallurgy 2013, 134, 11-18), phosphine sulfides (Ahmed et al., Int. J. Miner. Process. 2011, 101, 89-93), ketones (Hung et al. Solv. Extr. Ion Exch. 2007, 25, 407-416), thio and dithio-diglycolamides (Ruhela, et al., Tetrahedron Lett. 2011, 52, 3929-3932; Radiochimica Acta 2013, 101, 169-174) have also been presented as suitable extractants.

In a particular embodiment, the extractant is chosen from dimethyldibutyltetradecylmalonamide, bis-ethylhexyl sulfoxide or tributylphosphate.

In a preferred embodiment, said organic diluent is chosen from the group comprising aliphatic and apolar organic solvents, in particular linear and branched $C_5$-$C_{16}$ alkanes; petroleum ether; benzene and benzenes substituted by at least one linear or branched $C_1$-$C_4$ alkyl; kerosene; hydrogenated tetrapropylene (TPH); diethyl ether; n-butyl acetate; isopropyl myristate; and mixtures thereof.

Said linear and branched $C_5$-$C_{16}$ alkanes are in particular chosen from cyclopentane, pentane, cyclohexane, n-hexane, cycloheptane, n-heptane, n-octane, iso-octane, linear or branched nonane and dodecane, such as n-dodecane, hexadecane and mixtures thereof.

Said benzenes substituted by at least one linear or branched $C_1$-$C_4$ alkyl are in particular chosen from n-butylbenzene, isobutylbenzene, sec-butylbenzene, tert-butylbenzene, p-cymene, triisopropylbenzene, toluene, xylene, cumene and mixtures thereof.

A phase modifier may be admixed with the carrier solvent and the extractant to increase the solubility of the platinum group metal or gold, in particular palladium, and help prevent the formation of a third phase during extraction and when the platinum group metal or gold, in particular palladium, is stripped from the metal loaded organic extract phase. Water insoluble straight or branched chain aliphatic alcohols containing at least 6 carbon atoms in the hydrocarbon chain may generally be used as phase modifiers.

In a preferred embodiment, the phase modifier is chosen from isodecanol, 2-ethyl hexanol, 1-octanol, tridecanol and/or a mixture thereof, said phase modifier being in particular isodecanol. In a preferred embodiment, said second aqueous solution comprises more than 50%, more preferentially more than 55, 60, 65, 70, 75 or 80%, of the at least one metal chosen from the platinum group metals and gold, in particular Pd(II), comprised in the first organic liquid composition.

This percentage can for example be calculated using the following formula: ((weight of platinum group metal in the second aqueous solution)/(weight of platinum group metal in the first organic liquid composition))*100.

In a preferred embodiment, said second aqueous solution comprises less than 5%, more preferentially less than 4, 3 or 2%, of the organic diluent comprised in the first organic liquid composition.

This percentage can for example be calculated using the following formula: ((weight of organic diluent in the second aqueous solution)/(weight of organic diluent in the first organic liquid composition))*100.

In a preferred embodiment, said second aqueous solution comprises less than 2%, more preferentially less than 1.5, 1.0 or 0.5%, of the extractant comprised in the first organic liquid composition.

This percentage can for example be calculated using the following formula: ((weight of extractant in the second aqueous solution)/(weight of extractant in the first organic liquid composition))*100.

In a preferred embodiment, said second aqueous solution comprises more than 80%, more preferentially more than 82, 84, 86, 88, 90, 92, 94, 96 or 98%, of the surfactant comprised in the first aqueous solution.

This percentage can for example be calculated using the following formula: ((weight of surfactant in the second aqueous solution)/(weight of surfactant in the first aqueous composition))*100.

In a preferred embodiment, the concentration of the at least one metal chosen from the platinum group metals and gold, in particular Pd(II), in said first organic liquid composition is comprised from 100 to 10000 mg/L, more preferentially from 200 to 5000 mg/L.

In a preferred embodiment, the mass fraction of the surfactant in said first aqueous solution is comprised from 0.1 to 10% in weight, in particular from 0.2 to 5%, more particularly from 0.5 to 2% in weight, of said first aqueous solution.

In a preferred embodiment, the concentration of extractant in said first organic liquid composition is comprised from 0.05 to 5.0 mol/L.

In a preferred embodiment, the concentration of extractant in said first organic liquid composition is comprised from 0.3 to 0.7 mol/L, said extractant being in particular dimethyldibutyltetradecylmalonamide (DMDBTDMA).

In a preferred embodiment, the concentration of extractant in said first organic liquid composition is comprised from 0.10 to 0.25 mol/L, said extractant being in particular bis-ethylhexyl sulfoxide (BESO).

In a preferred embodiment, the mass fraction of extractant in said first organic liquid composition is comprised from 30 to 70% in weight of said first organic liquid composition, said extractant being in particular TBP.

In a preferred embodiment, the process as defined above further comprises, after step b), a step c) of performing a platinum group metal or gold-catalyzed reaction, in particular a palladium-catalyzed reaction, under micellar conditions by contacting said second aqueous solution with the reactants of said platinum group metal or gold-catalyzed reaction, in particular palladium-catalyzed reaction to obtain the product of the platinum group metal or gold-catalyzed reaction, in particular palladium-catalyzed reaction, under micellar conditions.

The palladium-catalyzed reaction is in particular a palladium cross coupling reaction, more particularly chosen from Suzuki-Miyaura, Buchwald-Hartwig, Heck, Heck-Matsuda, Sonogashira, Stille, Hiyama, Kumada, Negishi and Fukuyama reactions, in particular Suzuki-Miyaura and Buchwald-Hartwig reactions.

The gold-catalyzed reaction is in particular a gold-catalyzed cyclization.

The platinum group metal-catalyzed reaction is in particular metathesis, when the at least one metal chosen from the platinum group metals and gold is rhodium.

In a preferred embodiment, the first organic liquid composition is obtained by extracting an original aqueous phase comprising at least one metal chosen from the platinum group metals and gold, in particular Pd(II), more particularly an acidic aqueous phase comprising at least one metal chosen from the platinum group metals and gold, in particular Pd(II), with said extractant, optionally in presence of said organic diluent.

The extraction of said original aqueous phase comprising Pd(II) is well known from the one skilled in the art, and is for instance described in WO2016008932.

In a preferred embodiment, said at least one metal chosen from the platinum group metals and gold, in particular Pd(II), originates from mine ore, recycling of catalytic converters or wastes.

In a preferred embodiment, said at least one metal chosen from the platinum group metals and gold, in particular Pd(II), originates from an aqueous phase comprising nitric acid.

In a preferred embodiment, said second organic liquid composition of step a) is recovered.

In a particular embodiment, part or all of the recovered second organic liquid composition is recycled to extract said first aqueous solution comprising the at least one metal chosen from the platinum group metals and gold, in particular Pd(II).

In a preferred embodiment, the second organic liquid composition is subjected to steps a) and b) as defined above, in particular in a co-current or counter-current process.

In a preferred embodiment, said process is a continuous process.

In a preferred embodiment, said surfactant is a dendrimer of generation n comprising:
- an hydrophobic central core of valence m equal to 2 or 3;
- generation chains attached to the central core and branching around the core; and
- an hydrophilic terminal group at the end of each generation chain;

wherein n is an integer from 0 to 12;

the hydrophilic terminal group comprises:
- a mono-, oligo- or polysaccharide residue,
- a cyclodextrin residue,
- a polyethylene glycol (PEG) residue,
- a peptide residue,
- a tris(hydroxymethyl)aminoethane (Tris), or
- a 2-amino-2-methylpropane-1,3-diol;

the central core being a group of formula (Ia) or (Ib):

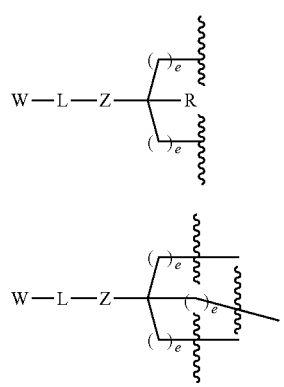

(Ia)

(Ib)

wherein:
W is $R_F$ or a group selected from $W_0$, $W_1$, $W_2$ or $W_3$:

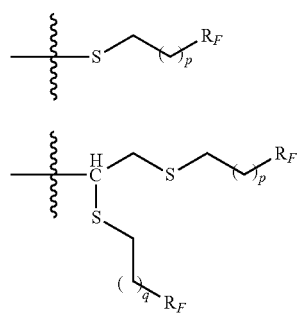

$W_0$ $W_1$

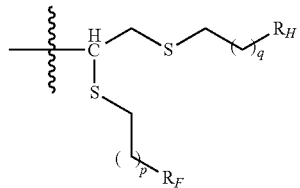

$W_2$

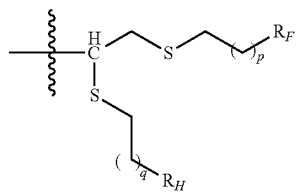

$W_3$ $R_F$ is a $C_4$-$C_{10}$ perfluoroalkyl or a $C_1$-$C_{24}$ alkyl group, $R_H$ is a $C_1$-$C_{24}$ alkyl group, p is 0, 1, 2, 3 or 4;

q is 0, 1, 2, 3 or 4;

L is a linear or branched $C_1$-$C_{12}$ alkylene group, optionally interrupted by one or more —O—, —S—, Z is C(=O)NH or NHC(=O), R is a $C_1$-$C_6$ alkyl group, and e is at each occurrence independently selected from 0, 1, 2, 3 or 4.

In one embodiment, $R_F$ is a $C_4$-$C_{10}$ perfluoroalkyl and $R_H$ is a $C_1$-$C_{24}$ alkyl group. In this case, the hydrophobic central core of the amphiphilic dendrimer does comprise a perfluoroalkyl group, and said dendrimer is herein referred to as fluorinated amphiphilic dendrimer.

In another embodiment, $R_F$ is a $C_1$-$C_{24}$ alkyl group and $R_H$ is a $C_1$-$C_{24}$ alkyl group. In this case, the hydrophobic central core of the amphiphilic dendrimer does not comprise a perfluoroalkyl group, and said dendrimer is herein referred to as hydrocarbon amphiphilic dendrimer.

In a particular embodiment, WL is a group selected from:

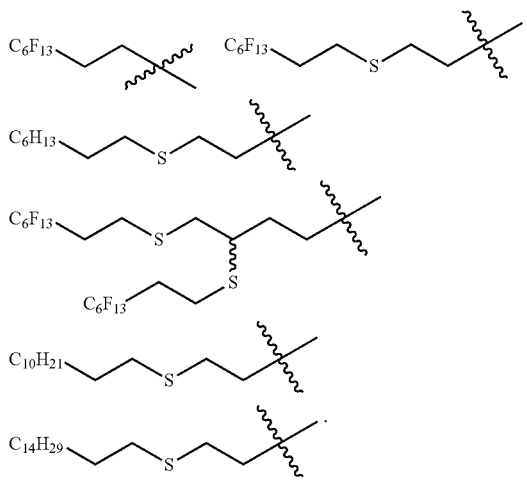

In a particular embodiment, each generation chain (n) branches via a group (a) or a group (b) as follows:

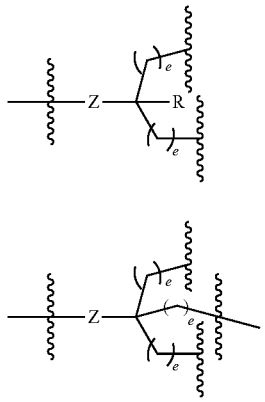

(a)

(b)

wherein

Z is C(=O)NH or NHC(=O),

R is a $C_1$-$C_6$ alkyl group, and e is at each occurrence independently selected from 0, 1, 2, 3 or 4.

In a particular embodiment, the terminal group comprises the following hydrophilic moieties:

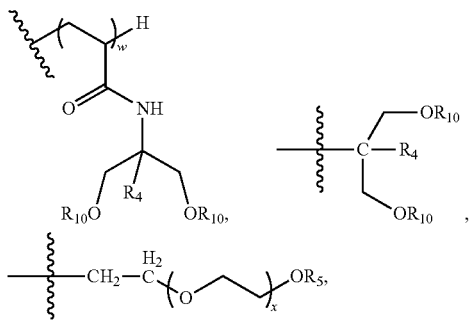

In a particular embodiment, the surfactant has the following formula:

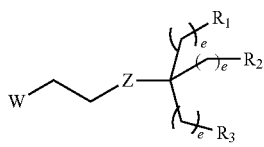

wherein:

W is $R_F$ or a group selected from:

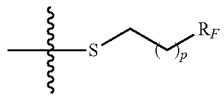

$W_0$

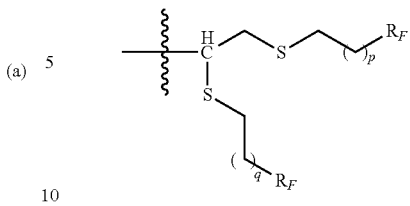

$W_1$

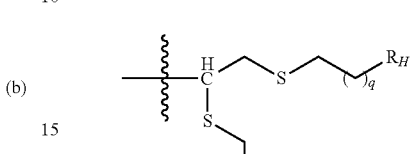

$W_2$

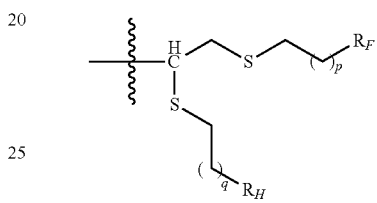

$W_3$ $R_F$ being a $C_4$-$C_{10}$ perfluoroalkyl or a $C_1$-$C_{24}$ alkyl group and $R_H$ being a $C_1$-$C_{24}$ alkyl group, p is 0, 1, 2, 3 or 4;

q is 0, 1, 2, 3 or 4;

Z is (CO)NH or NH(CO);

$R_1$, $R_2$, $R_3$ are H, or a group selected from (c) or (d):

$$X_a\text{---}(\text{---}V\text{---}X_a\text{---})_{k-1}V\text{---}X_a\text{---})_iY_a \qquad (c)$$

$$X\text{---}(\text{---}V\text{---}X_a\text{---})_{k-1}V\text{---}X_b\text{---})_jY_b \qquad (d)$$

provided that:

$R_1$, $R_2$, $R_3$ are the same and selected from either group (c) or (d) or one of $R_1$, $R_2$, $R_3$ is H, the two others being the same and selected from either group (c) or (d);

X is $X_a$ when j is 1 and $X_b$ when j is 0;

$X_a$ is at each occurrence independently selected from —OC(=O)CH$_2$—NH—, —OC(=O)CH$_2$—O—CH$_2$—, —O(CH$_2$)$_r$C(=O)—NH—, —O(CH$_2$)$_r$C(=O)—O—CH$_2$, OC(=O)NH—, —C(=O)—, —NH—, and —OCH$_2$—;

$Y_a$ is independently selected from:

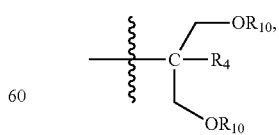

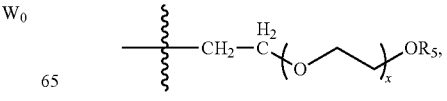

$X_b$ is

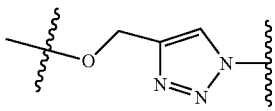 [SMILES: *OCc1cn(*)nn1]

$Y_b$ is independently selected from:

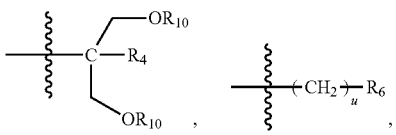

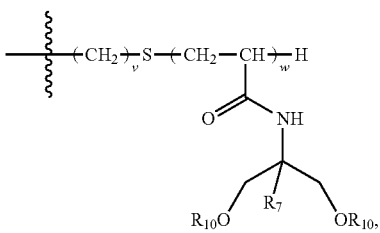

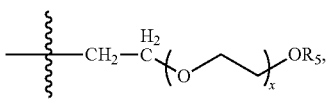

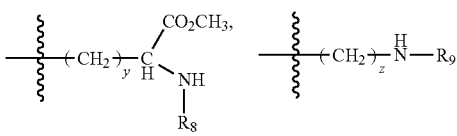

V is

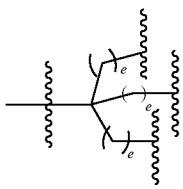

$R_4$, $R_7$ are each independently selected from H, $C_1$-$C_6$ alkyl and $CH_2OR_{10}$;

$R_5$ is selected from H and $C_1$-$C_6$ alkyl;

$R_6$ is a mono-, oligo-, polysaccharide or a cyclodextrine residue;

$R_8$, $R_9$ are each independently a peptide residue;

$R_{10}$ is H or a monosaccharide selected from glucose, galactose, mannose;

i is 0 or 1;

j is 0 or 1;

e is 0, 1, 2, 3 or 4;

k is an integer from 1 to 12, preferably 1, 2, 3, 4, or 5;

r is an integer from 1 to 10;

u is 0, 1, 2, 3 or 4;

v is 1, 2, or 3;

w is an integer from 1 to 20, preferably from 1 to 10;

x is an integer from 1 to 30, preferably from 5 to 15;

y, z are each independently an integer from 1 to 6.

In a particular embodiment, the hydrophilic terminal group of the surfactants defined above is of following formula:

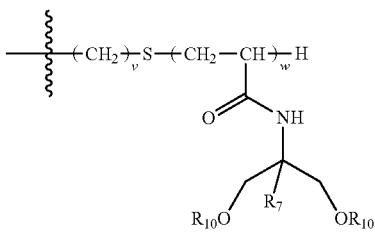

wherein $R_7$, $R_{10}$, v and w are as defined above, v being in particular equal to 3.

In a particular embodiment, the hydrophilic terminal group of the surfactants defined above is of following formula:

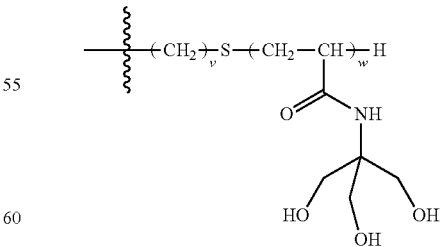

wherein v and w are as defined above, v being in particular equal to 3.

In a particular embodiment, the surfactant is selected from:
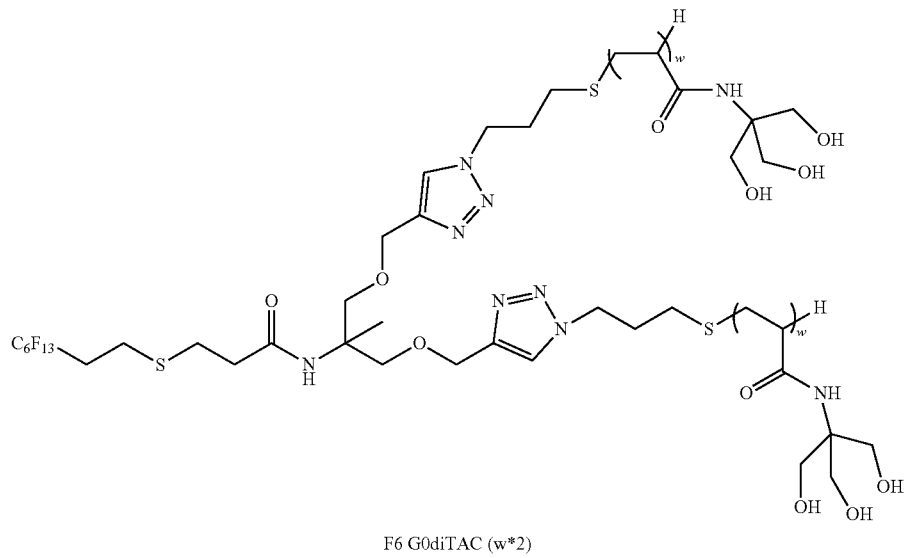
F6 G0diTAC (w*2)
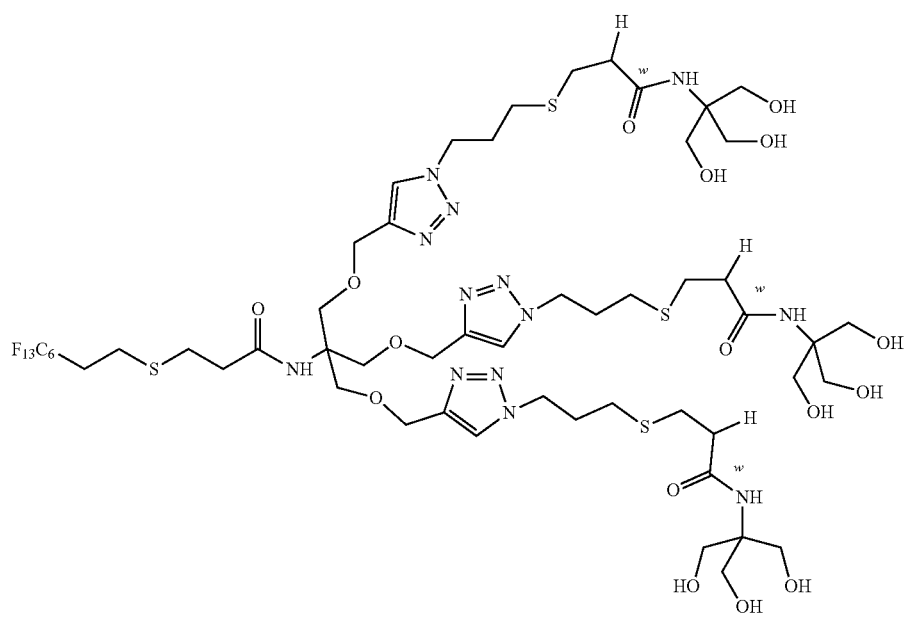
F6 G0 triTAC (w*3)

-continued
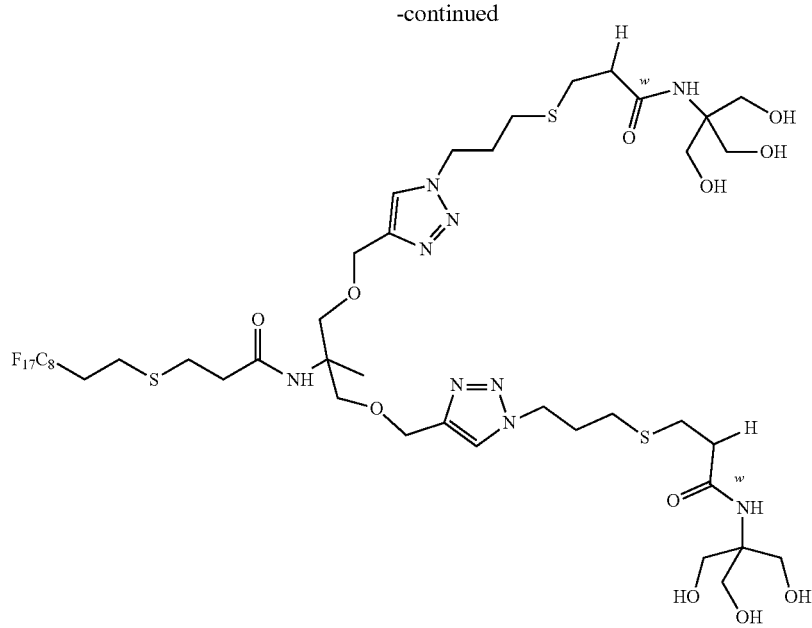
F$_8$ G$_0$ diTAC (w*2)
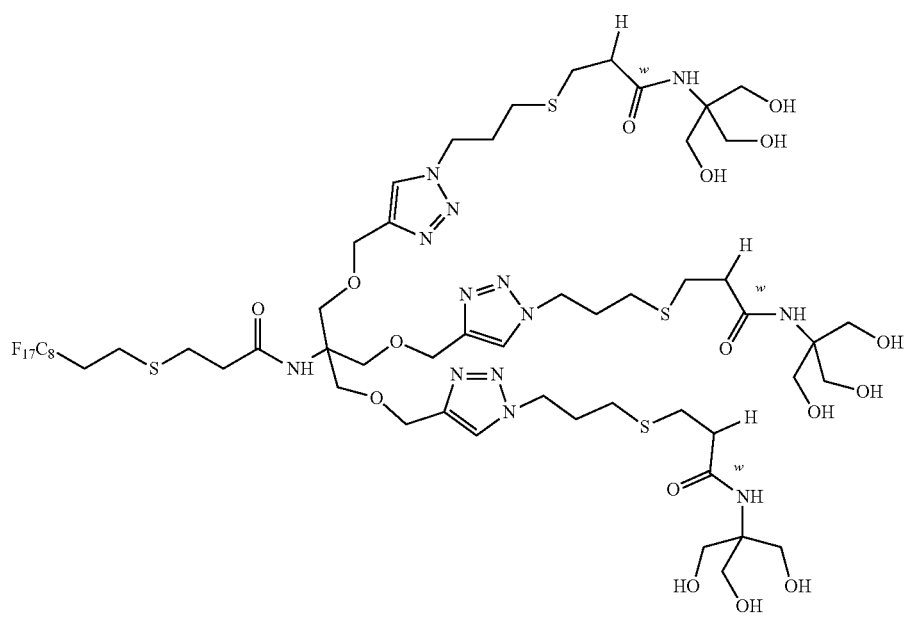
F$_8$ G$_0$ triTAC (w*3)

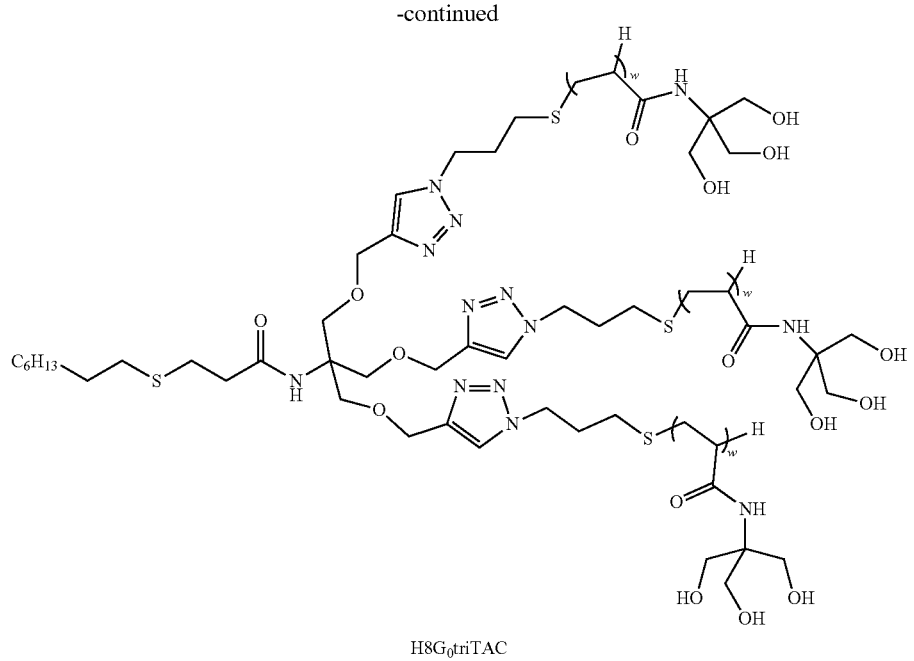
H8G₀triTAC
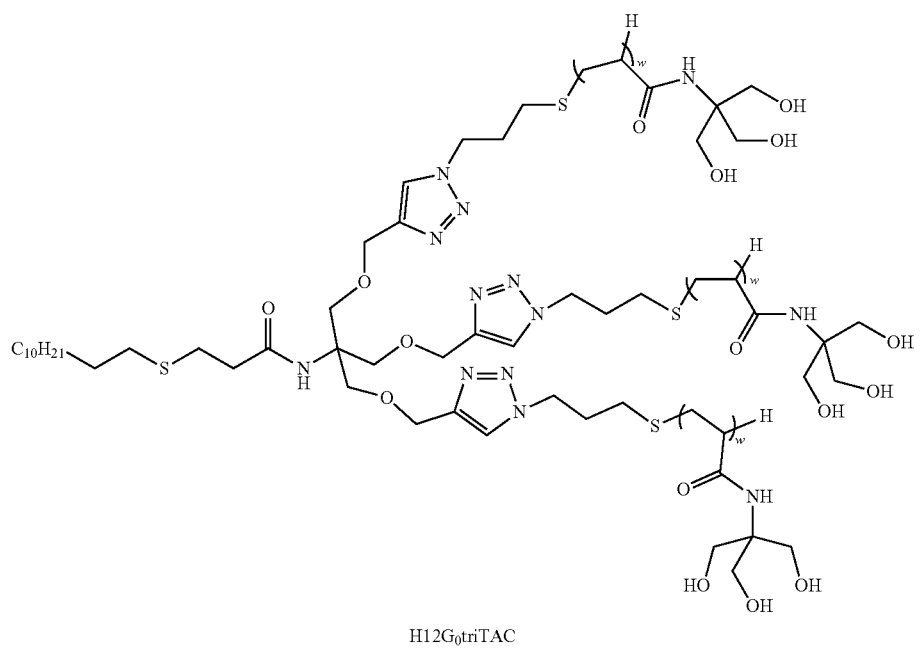
H12G₀triTAC

-continued
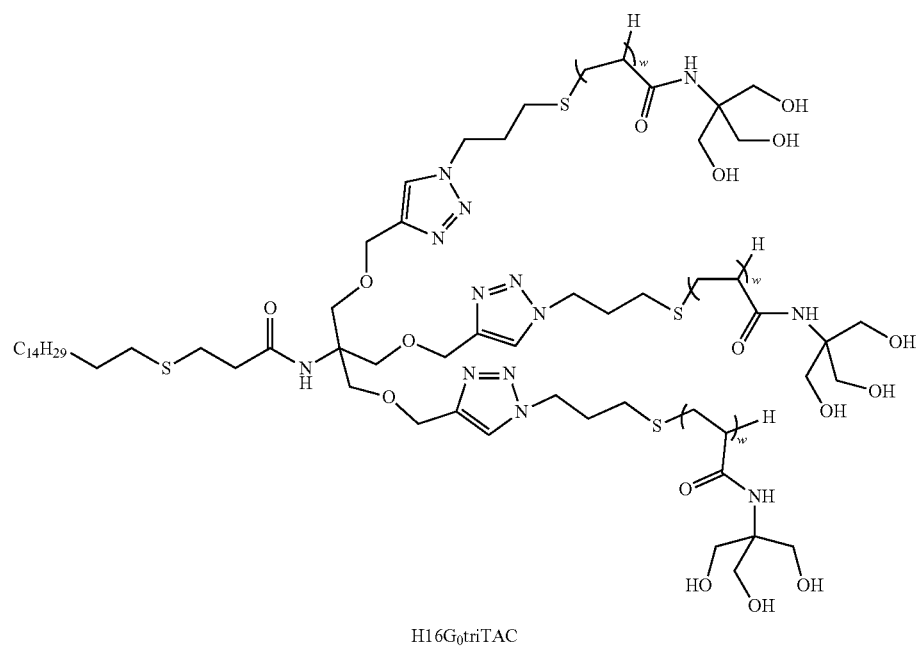
H16G₀triTAC
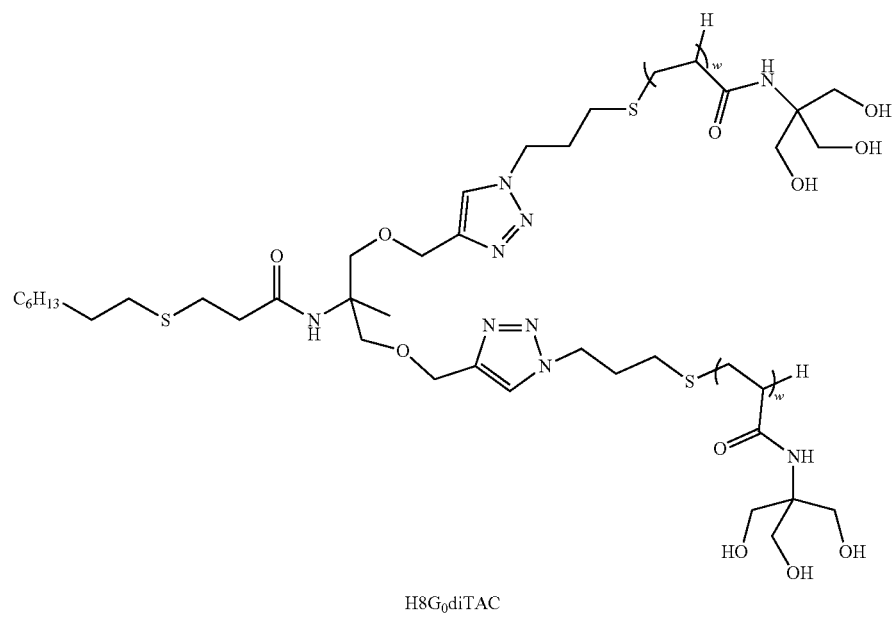
H8G₀diTAC

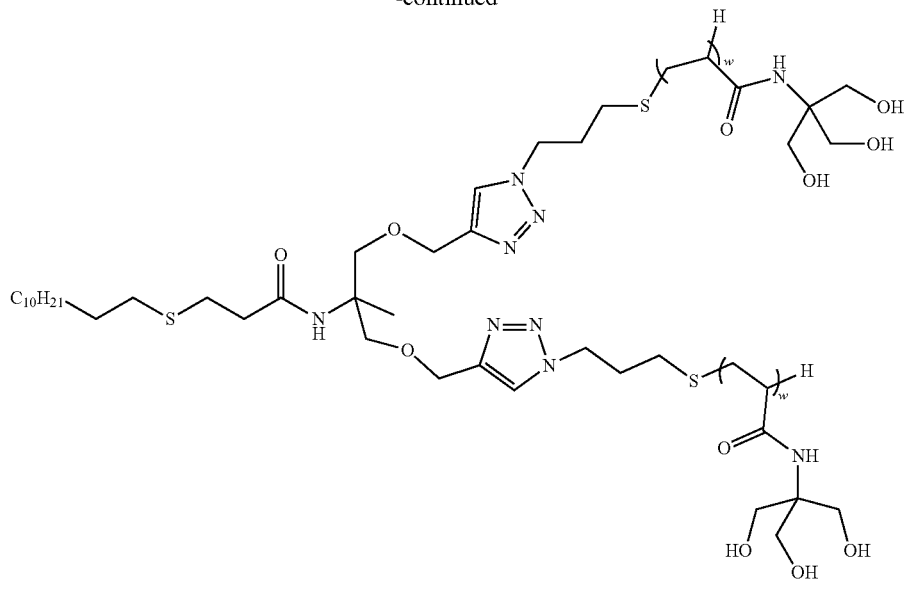

H12G₀diTAC

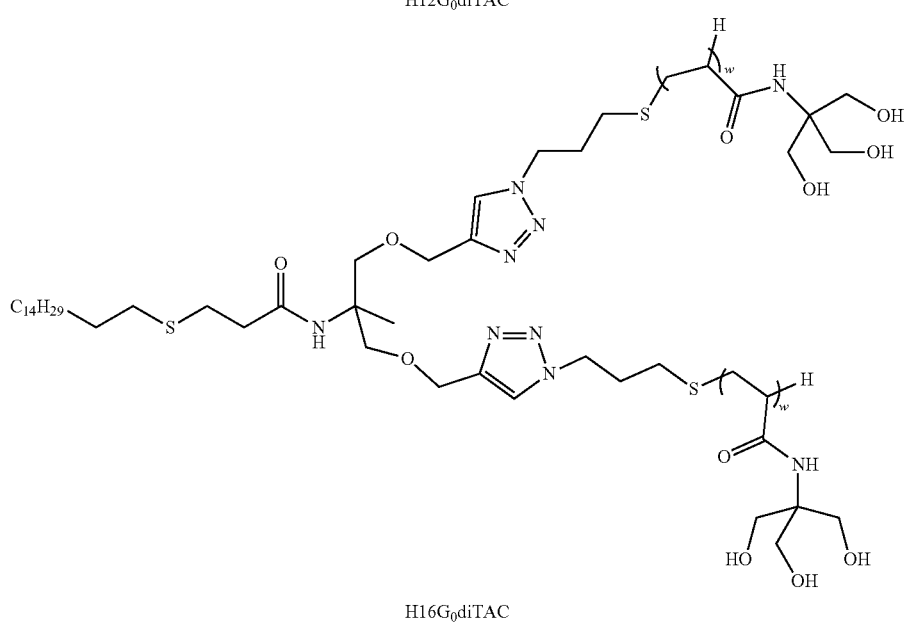

H16G₀diTAC wherein w is as defined above.

In a preferred embodiment, the surfactant is of formula (A):

$$W'\text{-}L'\text{-}G \quad \quad (A)$$

wherein
G is a hydrophilic group of the following formula:

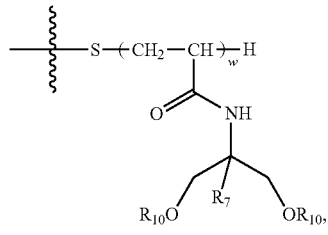

wherein:
$R_7$ is selected from H, $C_1$-$C_6$ alkyl and $CH_2OR_{10}$;
$R_{10}$ is H or a monosaccharide selected from glucose, galactose, mannose;
w is an integer from 1 to 30, preferably from 4 to 25;
W' is $R_F$ or a group selected from $W'_1$, $W'_2$ or $W'_3$:

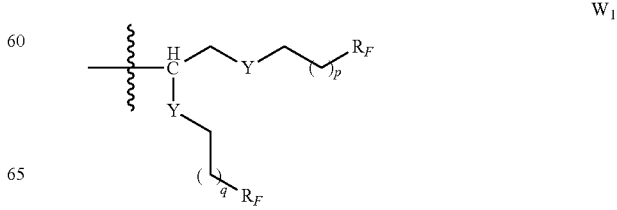

-continued

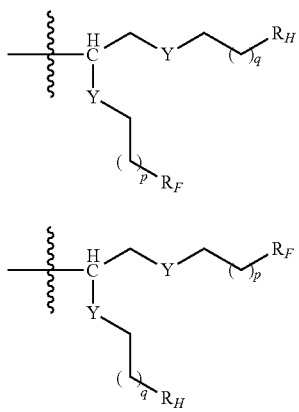

$R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L' is a linear or branched $C_1$-$C_{12}$ alkylene group, optionally interrupted by one or more groups Y';
Y' at each occurrence is chosen from —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH—, —O— or —S—;
Y at each occurrence is chosen from —S—, —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH— or —O—.

In one embodiment, $R_F$ is a $C_4$-$C_{10}$ perfluoroalkyl and $R_H$ is a $C_1$-$C_{24}$ alkyl group. In this case, the hydrophobic central core of the surfactant does comprise a perfluoroalkyl group, and said surfactant is herein referred to as F-TAC surfactants.

In another embodiment, $R_F$ is a $C_1$-$C_{24}$ alkyl group and $R_H$ is a $C_1$-$C_{24}$ alkyl group. In this case, the hydrophobic central core of the surfactant does not comprise a perfluoroalkyl group, and said surfactant is herein referred to as H-TAC surfactants.

In a particular embodiment, W'L' is a group selected from:

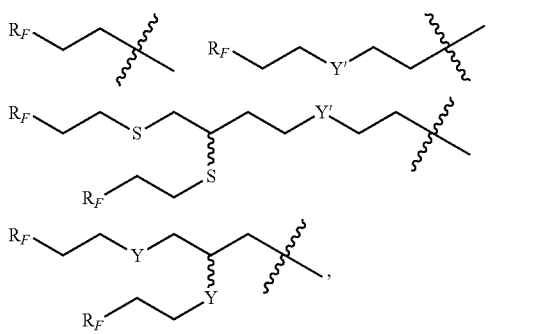

wherein $R_F$, Y and Y' are as defines above.
In a particular embodiment, Y is —S—, OC(=O)— or —C(=O)O—.
In a particular embodiment, Y' is —NHC(=O)— or —C(=O)—NH.

In a more particular embodiment, W'L' is a group selected from:

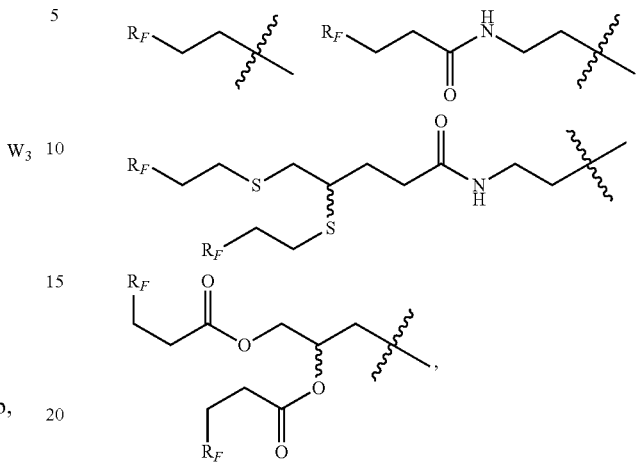

wherein $R_F$ is as defines above.
In an even more particular embodiment, W'L' is a group selected from:

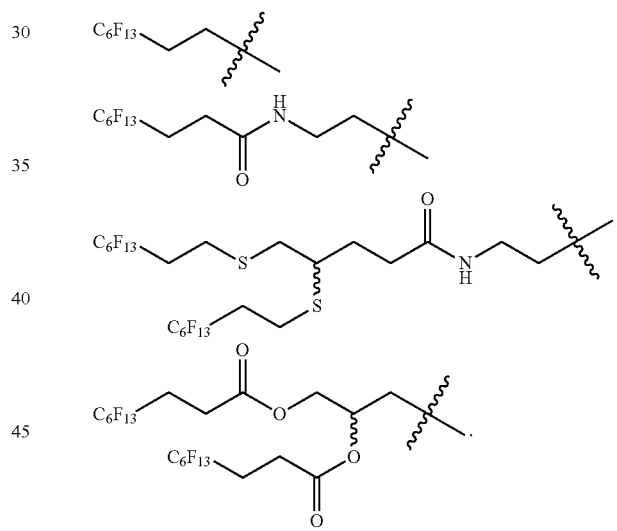

In a particular embodiment, the hydrophilic terminal group of the surfactants defined above is of following formula:

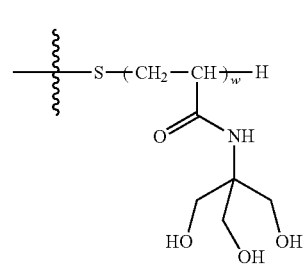

wherein w is as defined above.

In a particular embodiment, the surfactant is selected from:

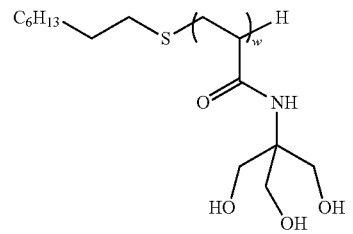

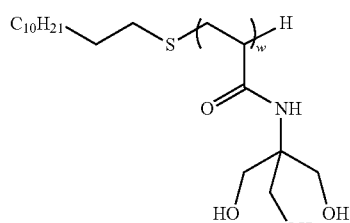

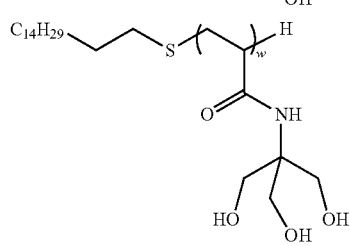

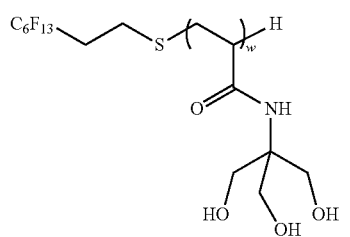

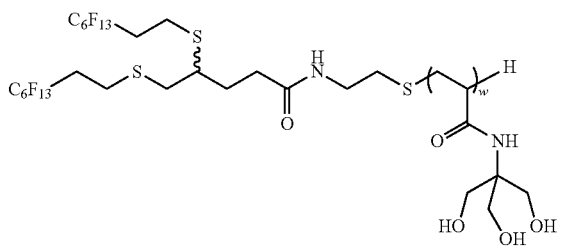

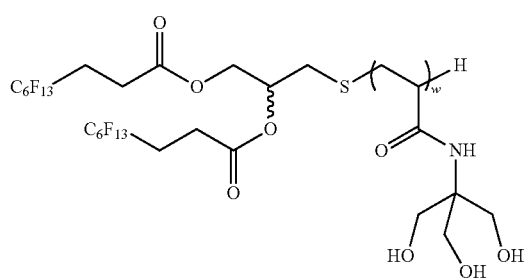

-continued wherein w is as defined above.

In another aspect, the present invention relates to a use of a surfactant as defined above for extracting at least one metal chosen from the platinum group metals and gold, in particular Pd(II), from a liquid composition to an aqueous solution, said liquid composition comprising:

at least one metal chosen from the platinum group metals and gold, in particular Pd(II), an organic solvent, said organic solvent being water immiscible.

Said extraction is in particular a liquid-liquid extraction, between the liquid composition and a first aqueous solution comprising said surfactant. A second aqueous solution is obtained after contacting said liquid composition and said first aqueous solution comprising said surfactant, and phase separation.

It is to be noted that the present invention includes the combination of all the embodiments listed hereabove, in particular for the solvent, the at least one metal chosen from the platinum group metals and gold, more particularly Pd(II), and the surfactant.

In another aspect, the present invention relates to a micelle comprising at least one metal chosen from the platinum group metals and gold, in particular Pd(II), and a surfactant as defined above.

It is to be noted that the present invention includes the combination of all the embodiments listed hereabove, in particular for the at least one metal chosen from the platinum group metals and gold, more particularly Pd(II), and the surfactant.

Such a micelle is in particular constituted by a core, and a shell comprising the surfactant, the hydrophobic core of said surfactant pointing to the core of the micelle, wherein the at least one metal chosen from the platinum group metals and gold, in particular Pd(II), is comprised in the core of the micelle and/or is complexed to the shell, more particularly to the hydrophilic groups of said shell.

In another aspect, the present invention relates to an aqueous solution comprising at least one metal chosen from the platinum group metals and gold, in particular Pd(II), and a surfactant as defined above.

It is to be noted that the present invention includes the combination of all the embodiments listed hereabove, in particular for the at least one metal chosen from the platinum group metals and gold, more particularly Pd(II), and the surfactant.

In another aspect, the present invention relates to an use of a micelle as defined above or an aqueous solution as defined above to perform a platinum group metal or gold-catalyzed reaction, in particular a palladium-catalyzed reaction, under micellar conditions.

In another aspect, the present invention relates to a amphiphilic dendrimer of generation n comprising:

an hydrophobic central core of valence m equal to 2 or 3;

generation chains attached to the central core and branching around the core; and an hydrophilic terminal group at the end of each generation chain;

wherein n is an integer from 0 to 12;

the hydrophilic terminal group comprises:

a mono-, oligo- or polysaccharide residue, a cyclodextrin residue, a polyethylene glycol (PEG) residue, a peptide residue, a tris(hydroxymethyl)aminoethane (Tris), or a 2-amino-2-methylpropane-1,3-diol;

the central core being a group of formula (Ia) or (Ib):

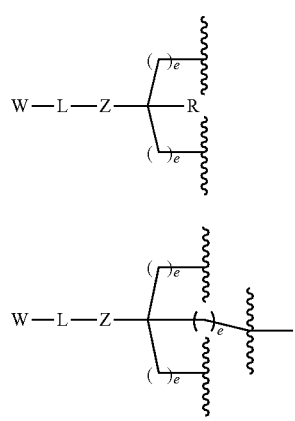

wherein:

W is $R_F$ or a group selected from $W_0$, $W_1$, $W_2$ or $W_3$:

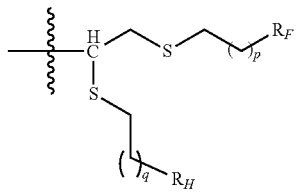

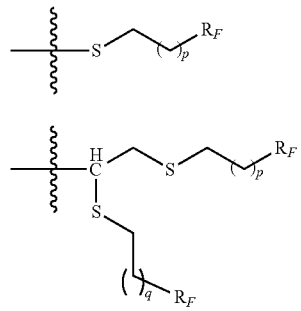

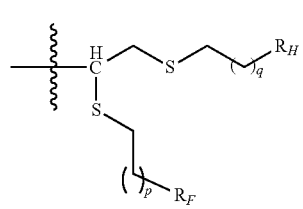

$R_F$ is a $C_1$-$C_{24}$ alkyl group, $R_H$ is a $C_1$-$C_{24}$ alkyl group, p is 0, 1, 2, 3 or 4;

q is 0, 1, 2, 3 or 4;

L is a linear or branched $C_1$-$C_{12}$ alkylene group, optionally interrupted by one or more —O—, —S—, Z is C(=O)NH or NHC(=O), R is a $C_1$-$C_6$ alkyl group, and e is at each occurrence independently selected from 0, 1, 2, 3 or 4.

It is to be noted that the present invention includes the combination of all the embodiments listed hereabove for the dendrimers.

In another aspect, the present invention relates to the use of a hydrocarbon amphiphilic dendrimer as defined above as a surfactant.

In another aspect, the present invention relates to a compound of formula (B):

$$W'\text{-}L'\text{-}G \quad (B)$$

wherein:

G is a hydrophilic group of the following formula:

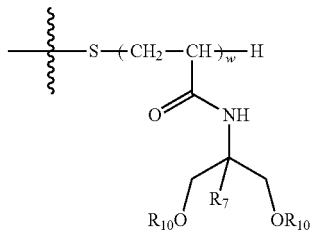

wherein:

$R_7$ is selected from H, $C_1$-$C_6$ alkyl and $CH_2OR_{10}$;

$R_{10}$ is H or a monosaccharide selected from glucose, galactose, mannose;

w is an integer from 1 to 30, preferably from 4 to 25;

W' is $R_F$ or a group selected from $W'_1$, $W'_2$ or $W'_3$:

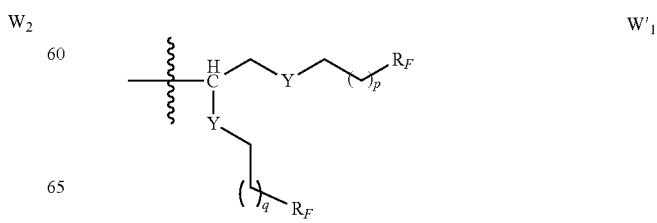

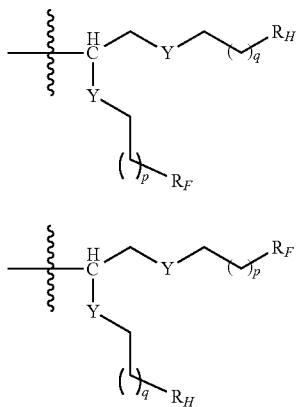

$R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L' is a linear or branched $C_1$-$C_{12}$ alkylene group, optionally interrupted by one or more groups Y';
Y' at each occurrence is chosen from —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH—, —O— or —S—;
Y at each occurrence is chosen from —S—, —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH— or —O—; provided that, when G is of formula

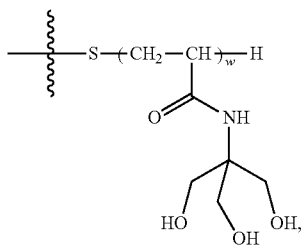

then L' is interrupted by one or more groups Y'.

In a particular embodiment, L' is interrupted by one or more groups Y'.

It is to be noted that the present invention includes the combination of all the embodiments listed hereabove for the compounds wherein m=1 (F- and H-TAC).

In another aspect, the present invention relates to the use of a compound of formula (B) as defined above as a surfactant.

Definitions

The following terms and expressions contained herein are defined as follows:

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein, the term "alkyl" refers to a straight-chain, or branched alkyl group having 1 to 24 carbon atoms, in particular 1 to 6, 10 or 12 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. A designation such as "$C_1$-$C_{10}$ alkyl" refers to an alkyl radical containing from 1 to 10 carbon atoms.

As used herein, the term "perfluoroalkyl" refers to a branched or straight hydrocarbon chain, in particular of 4 to 10 carbon atoms, in which the hydrogen atoms are replaced with fluorine atoms.

As used herein, the term "alkylene" refers to a branched or straight chained hydrocarbon of 1 to 6 carbon atoms, which is formed by the removal of two hydrogen atoms. A designation such as "$C_1$-$C_4$ alkylene" refers to an alkylene radical containing from 1 to 4 carbon atoms. Examples include methylene (—CH2-), 1,2-ethandiyl (—CH2CH2-), etc.

As used herein, the term "platinum group metal" refers to a metal chosen from palladium, platinum, rhodium, iridium, osmium or ruthenium, said metal being in particular palladium. Said platinum group metals and gold are in any of their oxidation states known in the art, in particular in the form of a salt or of a complex.

Said platinum group metal is in particular chosen from Pd(II), Pt(II), Pt(IV), Rh(III), Ir(III) or Ir(IV), and is more particularly Pd(II), Pt(II), Rh(III) or Ir(III), even more particularly Pd(II).

Gold is in particular Au(III).

As used herein, the term "Pd(II)" refers to a compound containing palladium having an oxidation state of +2. Said compound is in particular a salt based on $Pd^{2+}$ cation with $Cl^-$, $Br^-$, $I^-$, $NO^{3-}$ as counter anions, or a $[Pd(Cl)_4]^{2-}$ complex with $NH^{4+}$ or ammoniums as counter cations.

As used herein, the term "first organic liquid composition" refers to an organic liquid composition comprising at least one metal chosen from the platinum group metals and gold, in particular Pd(II), and an organic solvent, in particular a solution of the at least one metal chosen from the platinum group metals and gold, more particularly Pd(II), in the organic solvent.

As used herein, the term "organic solvent" refers to a liquid organic compound that dissolves the at least one metal chosen from the platinum group metals and gold, in particular Pd(II), and is water immiscible.

By "water immiscible" is meant a liquid unable to form a single phase with water at 25° C. and under atmospheric pressure, in the proportions implemented in the present invention, determined as the volumic ratio of aqueous phase vs organic phase, lying usually between 0.01 and 100, and more preferentially between 0.1 and 10.

As used herein, the term "extractant" refers to a compound able to extract the at least one metal chosen from the platinum group metals and gold, in particular Pd(II), from an acidic aqueous solution to an organic phase in the context of a liquid-liquid extraction.

As used herein, the term "organic diluent" refers to a liquid organic compound or a homogenous mixture of liquid organic compounds in which the extractant and optionally the phase modifier are dissolved.

In particular, the organic diluent by itself does not extract the at least one metal chosen from the platinum group metals and gold, in particular Pd(II), from an acid aqueous solution appreciably.

As used herein, the term "phase modifier" refers to a liquid organic compound or a homogenous mixture of liquid organic compounds added to the organic diluent to improve its properties, in particular by increasing the solubility of the extractant, changing interfacial parameters or reducing adsorption losses.

The first organic liquid composition and the first aqueous solution are contacted in the context of a liquid-liquid extraction.

As used herein, the term "second aqueous solution" refers to the aqueous phase formed when the aqueous and the organic phases obtained after the liquid-liquid extraction are separated.

As used herein, the term "second organic liquid composition" refers to the organic phase formed when the aqueous and the organic phases obtained after the liquid-liquid extraction are separated.

The extraction is referred to as the "back extraction", when the organic solvent comprises or consists of an extractant of the at least one metal chosen from the platinum group metals and gold, in particular Pd(II), from an acidic aqueous solution. In this context, the liquid composition may be obtained by extraction of at least one metal chosen from the platinum group metals and gold, in particular Pd(II), from an acidic aqueous solution, by said extractant.

FIGURES

FIG. 1 shows the results obtained after contacting an equal volume of toluene and aqueous (water+2 wt % surfactant) phases and shaking for 5 min at 20° C., in the conditions described in example 4. The surfactants SDS, TPGS-750-M and DendriTAC H12G$_0$diTAC (5*2) are respectively used.

EXAMPLES

General Procedure

All reagents were from commercial sources and were used as received. All solvents were distilled and dried according to standard procedures. Reactions were checked for completions by TLC (EM Science, silica gel 60 F 254) which were visualized by quenching of u.v. fluorescence ($\lambda_{max}$=254 nm) or by spraying a 5% sulphuric acid solution in ethanol or a 2% ninhydrin solution in ethanol, and then by heating at ~150° C. Flash chromatography were performed using silica gel 60 (40-63 µm, 230-400 mesh) or on combiflash Rf 200 apparatus from Teledyne Isco equipped with a UV detector. Size exclusion chromatography was carried out on hydroxypropylated cross-linked dextran (LH 20) from GE Healthcare. Fluorous solid-phase extractions were performed on Fluorochrom columns from SiliCycle®. HR-MS spectra were recorded on a mass spectrometer equipped with a TOF analyzer for ESI+experiments at the Laboratoire de Mesures Physiques of University Montpellier 2 (IBMM instrument platform).

NMR spectra were recorded on BRUCKER Avance 400 spectrometer. Samples were prepared in CDCL$_3$ (referenced to 7.26 ppm for $^1$H and 77.16 for $^{13}$C), DMSO-d6 (referenced to 2.51 ppm for $^1$H and 39.52 ppm for $^{13}$C), MeOD (referenced to 3.31 ppm for $^1$H and 49.00 ppm for $^{13}$C), D$_2$O (referenced to 4.79 ppm for $^1$H). Coupling constant (J) are in Hertz and corrected to the nearest 0.5 Hz. Multiplicities are reported as follows: s, singlet, d, doublet, dd, doublets of doublets, t, triplet, q, quartet, m multiplet, c, complex, and br broad pic. $^1$H NMR spectral assignments are supported by $^1$H-$^1$H COSY and $^{13}$C-$^1$H HSQC. Carbon spectra are supported by $^{13}$C-$^1$H HSQC analysis where necessary.

Example 1: Synthesis of Fluorinated Dendrimeric Surfactants 1.1. Synthesis of Oligomeric Hydrosoluble polyTRIS Moieties

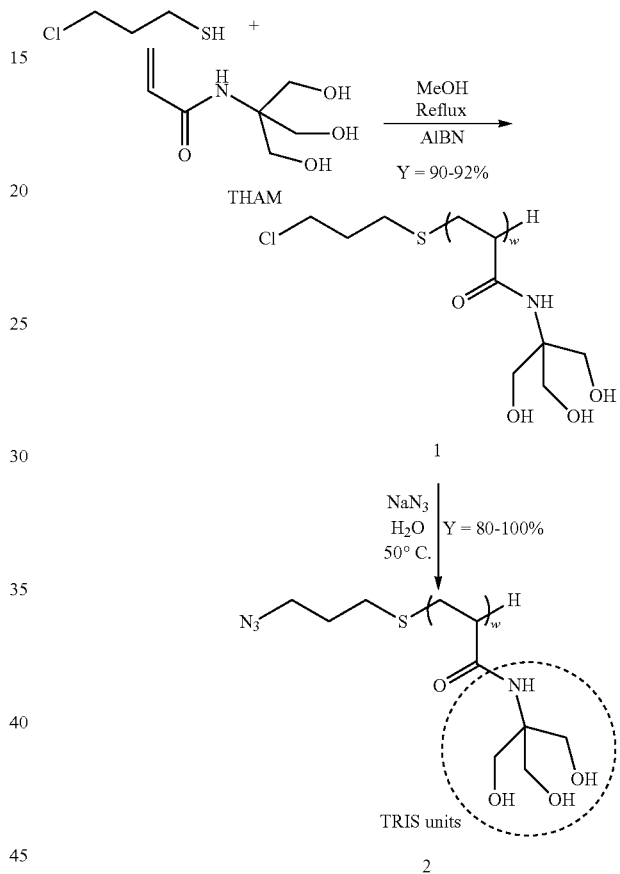

1.1.1. Synthesis of Chloro-polyTRIS Oligomer

Synthesis of Chloro-polyTRIS Oligomer 1a with DPn=9.4

To a solution of Tris(hydroxymethyl)acrylamidomethane (THAM) (8 g, 45.7 mmol, 12.5 eq) in dry and degassed MeOH under reflux, are added AIBN as radical initiator (60 mg, 0.365 mmol, 0.1 eq) and Chloropropanethiol as transfer reagent (354 µl, 3.65 mmol, 1 eq). The mixture is heated at reflux under nitrogen atmosphere until the total disappearance of the starting monomer THAM (monitored by TLC). Then the solution is filtered, concentrated and precipitated twice in Et$_2$O to give 1a (7.8 g) as a pure white compound (yield=92.8%). The DPn is assessed by 1H-NMR in MeOD, where the integral of the peak at 2.04 ppm is set for 2 protons (middle CH$_2$ of the CTA (chain transfer agent)), and by dividing the integral of the CH$_2$ protons of Tris(hydroxymethyl)aminomethane (TRIS) units at 3.80 ppm by six. DPn= (∫CH2 at 3.80 ppm)/6.

$^1$H NMR (MeOD, 400 MHz) δ, 3.80 (56H, br, CH$_2$—OH), 3.70 (2H, br, CH$_2$—C$_1$), 2.72-2.50 (4H, c, CH$_2$—

CH$_2$—CH$_2$—S, S—CH$_2$), 2.48-2.11 (5H, c, CH$_{OLIGOMER}$), 2.00 (2H, m, CH$_2$—CH$_2$—CH$_2$—S), 1.93-1.39 (8H, c, CH$_2$ $_{OLIGOMER}$).

Synthesis of Chloro-polyTRIS Oligomer 1b with DPn=5.2

To a solution of THAM (5 g, 28.6 mmol, 5 eq) in dry and degassed MeOH under reflux are added AIBN (374 mg, 0.228 mmol, 0.4 eq) and Chloropropanethiol (551 μl, 5.7 mmol, 1 eq). The mixture is heated at reflux under a nitrogen atmosphere until total disappearance of the starting monomer THAM (monitored by TLC). Then the solution is filtered, concentrated and precipitated twice in Et$_2$O to give 1b (5.24 g) as a pure white powder (yield=93.1%). The DPn is assessed by 1H-NMR in MeOD or D$_2$O, where the integral of the peak at 2.04 ppm is set for 2 Protons (middle CH$_2$ of the CTA (chain transfer agent)), and by dividing the integral of the CH$_2$ protons of TRIS at 3.80 ppm by six. DPn=(∫CH2 at 3.80 ppm)/6.

$^1$H NMR (D$_2$O, 400 MHz) δ, 4.02-3.71 (31H, br, CH$_2$—OH), 3.68 (2H, m, CH$_2$—C$_1$), 2.79-2.58 (4H, c, CH$_2$—CH$_2$—CH$_2$—S, S—CH$_2$), 2.56-2.11 (11H, c, CH$_{OLIGOMER}$), 2.04 (2H, br, CH$_2$—CH$_2$—CH$_2$—S), 1.93-1.39 (17H, c, CH$_2$ $_{OLIGOMER}$).

1.1.2. Synthesis of azido-polyTRIS oligomer

Synthesis of Azido-polyTRIS Oligomer 2a

To a solution of oligomer 1a (4 g, 2.1 mmol, 1 eq) in water (30 ml), is added NaN$_3$ (419 mg, 6.41 mmol, 3 eq). The reaction mixture is heated at 55° C., after 12H another 3 eq of NaN$_3$ is added and the solution is heated for another 12H. The solvent is removed under vacuum and the crude is purified over LH20 with pure MeOH. 3.77 g of 2a are recovered as a white powder (yield=94%). (D$_2$O, 400 MHz) δ, 3.90-3.59 (CH$_2$—OH), 3.44 (CH$_2$—N$_3$), 2.71-2.48 (CH$_2$—S—CH$_2$), 2.46-2.00 (CH$_{OLIGOMER}$), 1.84-1.25 (25H, c, CH$_2$—CH$_2$—CH$_2$—S, CH$_2$ $_{OLIGOMER}$).

Synthesis of Azido-polyTRIS Oligomer 2b

To a solution of oligomer 1b (4.23 g, 4 mmol, 1 eq) in water (30 ml), is added NaN$_3$ (780 mg, 12 mmol, 3 eq). The reaction mixture is heated at 55° C., after 12H another 3 eq of NaN$_3$ are added and the solution is heated for another 12H. The solvent is removed under vacuum and the crude is purified over LH20 with pure MeOH. 3.4 g of 2b are recovered (yield=80%). (D$_2$O, 400 MHz) δ, 3.91-3.74 (CH$_2$—OH), 3.44 (CH$_2$—N$_3$), 2.77-2.58 (—CH$_2$—S—CH$_2$), 2.56-2.11 (CH$_{OLIGOMER}$), 1.93-1.44 (CH$_2$—CH$_2$—CH$_2$—S, CH$_2$ $_{OLIGOMER}$).

1.2. Amphiphilic Dendrimers Functionalized with polyTris Moieties-Generation 0 (G$_0$)

1.2.1. Synthesis of the Monocatenar Scaffold (Mickaël Addition) F6G$_0$ (AB2)

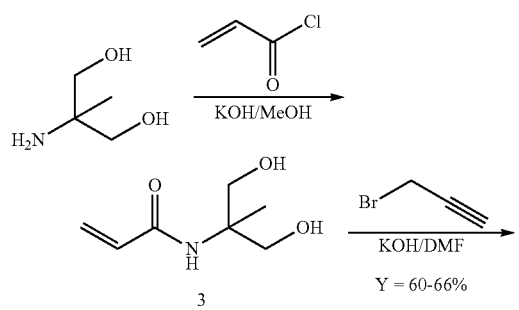

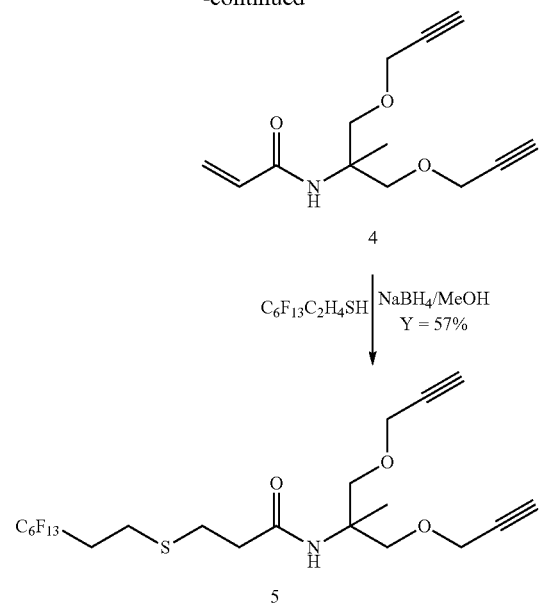

Synthesis of compound N-(1,3-dihydroxy-2-methylpropan-2-yl)acrylamide (3)

This synthesis was already described in Journal of fluorine chemistry by M. Abla, G. Durand, C. Breyton, S. Raynal, C. Ebel, B. Pucci, J. Fluor. Chem. 134, 63 (2012).

Synthesis of compound N-(2-methyl-1,3-bis(prop-2-yn-1-yloxy)propan-2-yl)acrylamide (4)

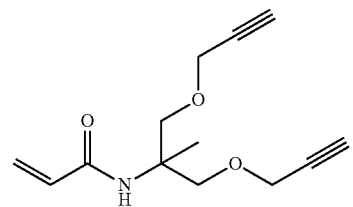 [SMILES: C#CCOCC(C)(COCC#C)NC(=O)C=C]

To a solution of 3 (1 eq, 2.00 g, 13 mmol) and propargyl bromide (2.3 eq, 3.27 ml, 30 mmol) dissolved in 40 ml of dry DMF and cooled at 0° C., is added finely grinded KOH (2.1 eq, 1.50 g, 26 mmol) in portions over a period of one hour. The reaction mixture is left to warm and stirred overnight at room temperature. The mixture is diluted with 200 ml of EtOAc and washed 4 times with water. All organic phases are pooled, dried over Na$_2$SO$_4$ and concentrated in vacuo to dryness. The crude product is purified by silica gel column chromatography (cyclohexane/EtOAc 9:1-7:3 as eluent) to afford 1.48 g of pure 4 as a white powder (yield=50%). TLC Rf=0.3 (Cyclohexane/Ethyl acetate 7/3).

$^1$H NMR (CDCl$_3$, 400 MHz) δ 6.24-6.11 (3H, m, CH$_2$=CH, NH), 5.58 5.58 (1H, dd, J=4.0, 2.0 Hz CH 4.16 (3H, s, CH$_2$), 4.24-4.27 (1H, t, J=6.2 Hz), 2.53 (2H, t, J=4.0 Hz), 1.43 (3H, s, CH$_3$); 13C NMR (CDCl$_3$, 100 MHz) δ 165.10 (C=O), 131.78.67 (CH$_2$=CH), 125.72 (CH$_2$=CH), 79.44 (CH), 74.76 (CH), 71.70 (CH$_2$—O), 58.38 (CH$_2$—C), 56.28 (C), 18.96 (CH$_3$) ESI Calcd for C$_{13}$H$_{18}$NO$_3$: 236.13 [M+H$^+$], found m/z 236.13 [M+H$^+$]. HRMS Calcd for C$_{13}$H$_{18}$NO$_3$: 236.1287 [M+H$^+$], found m/z 236.1293 [M+H$^+$].

Synthesis of compound N-(2-methyl-1,3-bis(prop-2-yn-1-yloxy)propan-2-yl)-3-((3,3,4,4,5,5,6,6,7,7,8,8,8-tridecafluorooctyl)thio)propanamide (5)

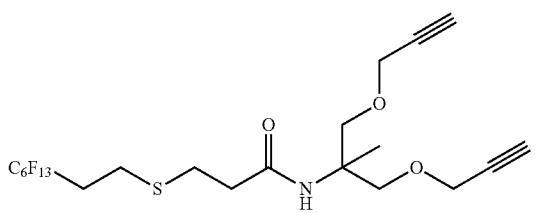

NaBH$_4$ (396 mg, 10.6 mmol, 2.5 eq) is added by portion to a cold solution of 1H, 1H, 2H, 2H perfluorooctanethiol (1.70 g, 4.46 mmol, 1.05 eq) in dry methanol (10 ml). The reaction mixture is stirred for 30 mn at 0° C. Then this solution is carefully added to a solution of 4 (1 g, 4.25 mmol, 1 eq) in dry methanol (90 ml) and the resulting mixture is stirred for 24 h. After 24 h another 0.5 eq of 1H, 1H, 2H, 2H perfluorooctanethiol and NaBH$_4$ are added in the same way as previously and the mixture is stirred for another 24 h. The solvent is evaporated in vacuo to dryness, the crude is purified over silica gel (cyclohexane/EtOAc 9:1-7:3 as eluent) to afford compound 5 (1.50 g, yield=57%) as a pure product. TLC Rf=0.42 (Cyclohexane/Ethyl acetate 7/3).

$^1$H NMR (CDCl$_3$, 400 MHz) δ (5.81 (1H, NH, s), 4.16 (4H, d, J=2.5 Hz CH$_2$-Alkyne), 3.62 (2H, d, J=9 Hz, CH$_2$—O), 3.50 (2H, d, J=9.0 Hz, CH$_2$—O), 2.82 (2H, t, J=7.0 Hz), 2.74 (2H, t, J=9.0 Hz (CH$_2$—S), 2.38-2.20 (6H, m, CF$_2$—CH$_2$, CH, CH$_2$—C=O), 1.29 (3H, s, CH$_3$); $^{13}$C NMR (CDCl$_3$, 100 MHz) δ 170.63 (C=O), 79.48 (CH), 74.63 (CH), 71.91 (CH$_2$—O), 58.52 (CH$_2$—C), 56.22 (C), 37.17 (CH$_2$—C=O), 31.99 (CH$_2$—CF$_2$), 27.60 (CH$_2$—S), 22.80 (CF$_2$—CH$_2$), 19.04 (CH$_3$); $^{19}$F NMR (CDCl$_3$, 100 MHz) −81.44 (3H, t, J=10.0 Hz), −114.70 (2H, q, J=15.0 Hz), −122.32 (2H, br s, J=12.0 Hz), −123.32 (2H, br s), −123.76 (2H, br s), −126.66 (2H, br s). ESI Calcd for C$_{21}$H$_{23}$F$_{13}$NO$_3$S: 616.12 [M+H$^+$], found m/z: 616.12 [M+H$^+$]. HRMS Calcd for C$_{21}$H$_{23}$F$_{13}$NO$_3$S: 616.1191 [M+H$^+$], found m/z 616.1191 [M+H$^+$].

1.2.2. Functionalization with Hydrophilic PolyTris Moieties

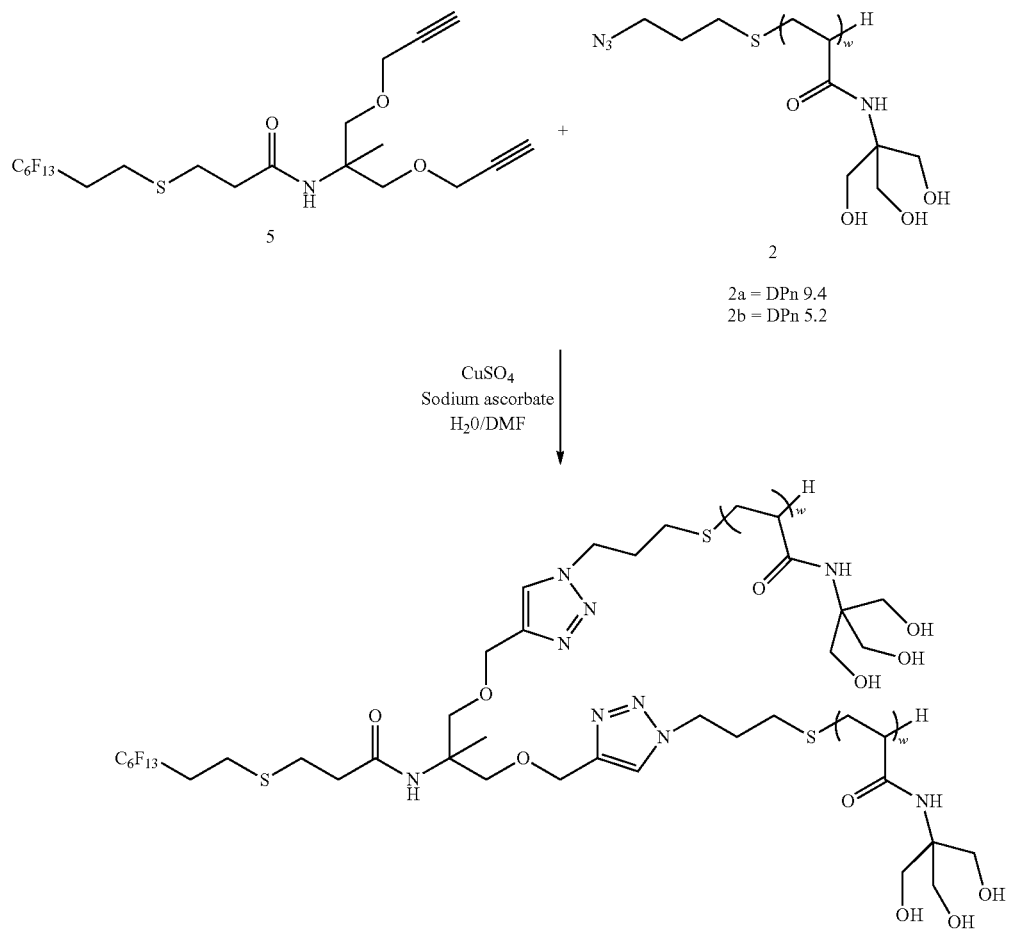

Y = 72.5% for F6 G0 diTAC (10*2)
Y = 19.8% for F6 G0 diTAC (7*2)

a—Synthesis of F6 G₀diTAC (10*2)

Sodium ascorbate (169 mg, 0.85 mmol, 1.2 eq), compounds 5 (438 mg, 0.732 mmol, 1 eq) and 2a (3.71 g, 2 mmol, 2.8 eq) (DPn=9.4) are dissolved in DMF (40 ml), the reaction mixture is heated at 50° C., and after 5 minutes copper sulfate pentahydrate (71 mg, 0.28, 0.2 eq) is added. The solution is heated overnight. The solution is filtered and passed through chelex beads, and then the solvent is evaporated under vacuum. The crude is dissolved in a mixture of MeOH/water 9/1, filtered and purified over LH20 MeOH/H₂O 9/1. The purification is followed by TLC (Ethyl Acetate/MeOH 5/5): only fractions with a spot staying at the start were recovered. The solvent is carefully removed in vacuo at a temperature about 0° C. at the beginning and then at room temperature out of the water bath, then diluted with water and freeze dried. The product is further purified by fluorous solid-phase extraction (FSPE). Briefly, the column is equilibrated with 25 ml of a mixture of water and DMF (9/1), then between 100 mg and 400 mg of product are dissolved in 1 ml of this mixture and deposit onto the column, after 25 ml of this eluent is pass through the column to get rid of non-fluorous compounds, then 25 ml of water, followed by 25 ml of a mixture of MeOH and Water (9/1) and finally 25 ml of pure methanol in order to rinse the column. Eluents containing methanol are concentrated in vacuo, dilute with water and freeze dried in order to obtain a fluffy white powder. We obtain 2.25 g of compound F6 G₀diTAC (10*2) with a DPn of 10; yield=72.5%.

The DPn is assessed by 1H-NMR in DMSO, where integrals of peaks at 4.40 and 4.49 ppm are set for 8 Protons (Two CH₂ in a position of the triazole ring), and by dividing the integral of the CH₂ protons of TRIS at 3.80 ppm by six or dividing the integral of the OH protons, between 5.48 and 4.64 ppm, by three.

$^1$H NMR (DMSO-d6, 400 MHz) δ (8.07 (2H, s, CH triazole), 7.75-6.85 (25H, c, NH), 5.48-4.64 (70H, c, OH), 4.49 (4H, s, $C_{TRIAZOLE}$—CH₂—O), 4.40 (4H, s, CH₂—CH₂—$N_{TRIAZOLE}$), 3.94-3.40 (143H, br, CH₂—OH, CH₂—O—), 2.71 (4H, c, CF₂—CH₂—CH₂—S, S—CH₂—CH₂—C=O), 2.50 (2H, c, CF₂—CH₂), 2.45 (2H, br, CH₂—CH₂—CH₂—S), 2.36 (2H, t, J=7.54 Hz, CH₂—C=O), 2.29-1.84 (29H, c, CH₂—CH₂—CH₂—S, CH₂—S, CH, CH₂—C=O, CH—C=O$_{OLIGOMER}$), 1.80-1.28 (38H, M, CH$_{2OLIGOMER}$), 1.18 (3H, S, CH₃); $^{13}$C NMR (DMSO-D6 100 MHZ) δ 175.68 (C=O oligomer), 170.46 (C=O), 144.01 (C-triazole), 123.79 (CH-triazole), 71.54 (CH₂—O), 64.01 ($C_{TRIAZOLE}$—CH₂—O), 62.35 (C), 60.53 (CH₂—OH) 56.36 (C), 48.16 (CH₂—Ntriazole), 42.16 (C-oligomer), 41.59 (C-oligomer), 36.06 (CH₂—C=O), 31.13 (CH₂—CF₂), 28.27 (CH₂—CH₂—CH₂—S), 26.97 (CF₂—CH₂—CH₂—S), 21.77 (S—CH₂—CH₂—C=O), 19.23 (CH₃); $^{19}$F NMR (DMSO-d6, 100 MHz) −80.19 (3H, t, J=8.68 Hz), −113.22 (2H, br), −121.73 (2H, br), −122.65 (2H, br), 122.65 (2H, br) −125.74 (2H, br).

b—Synthesis of F6 G₀diTAC (7*2)

Sodium ascorbate (285 mg, 1.44 mmol, 1.2 eq), compounds 5 (742 mg, 1.2 mmol, 1 eq) and 2 (3.82 g, 3.62 mmol, 3 eq) (DPn-5) are dissolved in mixture of DMF (100 ml) and water (100 ml), the reaction mixture is heated at 60° C., and after 5 minute copper sulfate pentahydrate (120 mg, 0.48, 0.2 eq) is added. The solution is heated at 60° C. during 3 hours and stirred at room temperature overnight. The solution is filtered and passed through chelex beads, and then the solvent is evaporated under high vacuum. The crude is dissolved in a mixture of MeOH/water 9/1 and filtered and then purified over LH20 MeOH/Water 9/1. The purification is followed by TLC (Ethyl Acetate/MeOH 5/5): only fractions with a spot staying at the start were recovered. The solvent is carefully removed in vacuo at a temperature about 0° C. at the beginning and then at room temperature without the water bath. The mixture is diluted with water, freeze dried and further purified by FSPE as previously described to give 650 mg of compound F6 G₀diTAC (7*2) with a DPn of 7; y=19.8%. The DPn was assessed by 1H-NMR as previously described for F6 G₀diTAC (10*2).

$^1$H NMR (DMSO-d6, 400 MHz) δ (8.06 (2H, s, CH triazole), 7.75-6.81 (20H, c, NH), 5.48-4.62 (58H, c, OH), 4.50 (4H, s, $C_{TRIAZOLE}$—CH₂—O), 4.41 (4H, s, CH₂—CH₂—$N_{TRIAZOLE}$), 3.77-3.47 (122H, br, CH₂—OH), 2.29-1.84 (28H, c, CH₂—S, CF₂—CH₂, CH, CH₂—C=O, CH—C=O$_{OLIGOMER}$), 1.80-1.28 (36H, m, S—CH$_{2OLIGOMER}$), 1.24 (3H, s, CH₃); $^{19}$F NMR (DMSO-d6, 100 MHz) −80.44 (3H, br), −113.34 (2H, q, J=15.0 Hz), −121.92 (2H, br), −122.88 (4H, br), −125.97 (2H, br).

Example 2: Synthesis of Hydrocarbon Dendrimeric Surfactants 1.1. Synthesis of the Monocatenar Scaffold (Via Mickaël Addition) with Different Hydrocarbon Chain Lengths (AB3 Building Blocks)

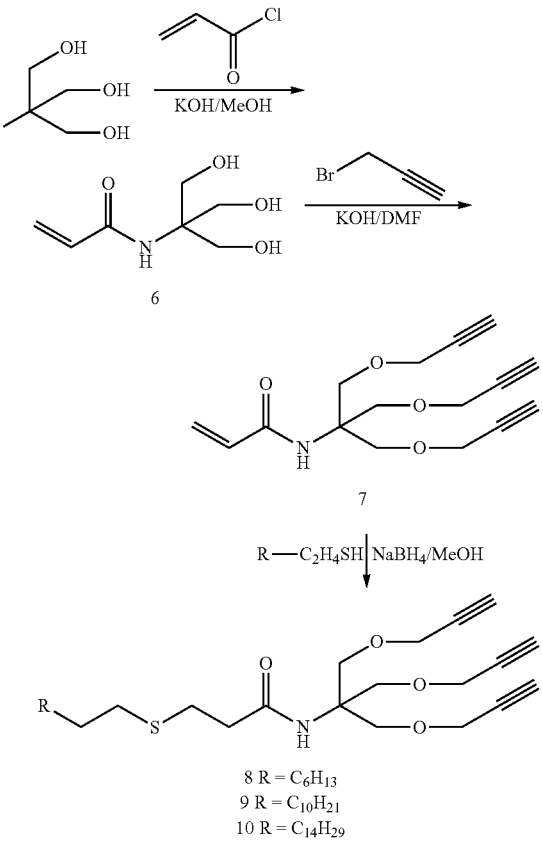

a) Synthesis of Tris(hydroxymethyl)acrylamidomethane (compound 6)

Synthesis of compound 6 was performed using the procedure described by Pucci et al. (*Eur. Polym. J.*, 1991, 27, 1101). To a stirred solution of tris(hydroxymethyl)aminomethane (3.00 g, 24.8 mmol) in methanolic potassium hydroxide 3N, at 0° C. within a pH range between 8 and 9, acryloyl chloride (3.60 ml, 44.6 mmol) was added dropwise. The reaction mixture was stirred at 0° C. for 1 h and then allowed to warm up to room temperature. After 4 h, the reaction mixture was filtered and the filtrate evaporated in vacuo to dryness. After precipitation and recrystallization from methanol, the desired compound 6 was obtained (3.78 g, 87%) as a white powder. m.p. 136° C.; $v_{max}$(NaCl)/cm$^{-1}$ 3420s (br), 1653s, 1560m, 1540m, 1018m; $\delta_H$ (300 MHz; DMSO-d$_6$) 3.56 (d, 6H, J 5.7, CH$_2$), 4.76 (t, 3H, J 5.7, OH), 5.54 (dd, 1H, J 2.4, J 9.9, H$_a$), 6.02 (dd, 1H J 2.4, J 17.1 Hz, H$_b$), 6.37 (dd, J 9.9, J 17.1, H$_c$), 7.42 (s, 1H, NH); $\delta_c$ (75.5 MHz; DMSO-d$_6$) 60.6, 62.6, 125.2, 132.4, 165.5.

b) Synthesis of N-acryloyl-tris[(propargyloxy) methyl]aminomethane (compound 7)

A solution of tris(hydroxymethyl)acrylamidomethane 6 (500 mg, 2.85 mmol) in anhydrous DMF (10 mL) was stirred at 0° C. with propargyl bromide (80 wt. % in Toluene 1.10 mL, 12.85 mmol). Portions of finely ground KOH (960 mg, 17.14 mmol) were added over a period of 30 min. The reaction mixture was stirred at r.t. and the course of the reaction was monitored by TLC (EtOAc/MeOH 7:3) until complete disappearance of 6. The mixture was concentrated to dryness and the residue partitioned between ethyl acetate (200 mL) and brine (200 mL). The organic layer was washed with water, dried with Na$_2$SO$_4$ and the solvent removed at reduce pressure to give the crude product, which was purified by flash chromatography (Hexanes/EtOAc 70:30). After crystallization from ethyl acetate/hexanes, compound 7 was obtained (0.630 g, 76%) as colorless needles. Rf (EtOAc/Hexanes 7:3)=0.65; m.p. 85° C. (from EtOAc/ Hexanes). $v_{max}$(NaCl)/cm$^1$ 3300s (br), 2124s, 1658s, 1623s, 1555s, 1101s, 799s (br); $\delta_H$ (300 MHz; CDCl$_3$) 2.44 (t, 3H, J 2.4, C≡CH), 3.89 (s, 6H, C$_q$CH$_2$O), 4.15 (d, 6H, J 2.4, OCH$_2$C≡CH), 5.58 (dd, 1H, J 1.8, J 9.9, H$_a$), 5.86 (s, 1H, NH), 6.06 (dd, 1H, J 9.9, J 17.1, H$_c$), 6.23 (dd, 1H, J 1.8, J 17.1, H$_b$); $\delta_C$ (75.5 MHz; CDCl$_3$) 58.6, 59.3, 68.4, 74.7, 79.5, 126.3, 131.4, 165.3; m/z (TOF$^+$ HRMS) for C$_{16}$H$_{19}$NO$_4$: 290.13868 [M+H]$^+$, found 290.13916; 312.12063 [M+Na]$^+$, found 312.12096.

c) Synthesis of Compound N-(1,3-bis(prop-2-yn-1-yloxy)-2-((prop-2-yn-1-yloxy)methyl)propan-2-yl)-3-(octylthio)propanamide (compound 8 R=C$_6$H$_{13}$)

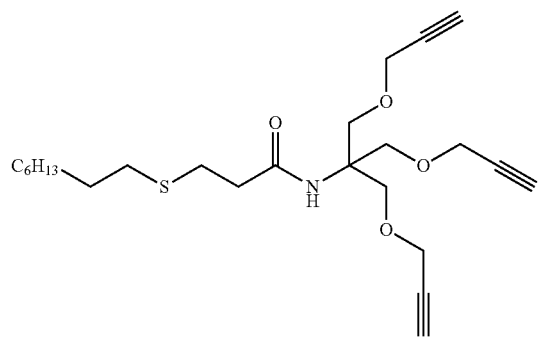

8

NaBH$_4$ (327 mg, 8.65 mmol, 2.5 eq) is added by portion to a cold solution of octanethiol (0.53 g, 3.63 mmol, 1.05 eq) in dry methanol (10 ml). The reaction mixture is stirred for 30 mn at 0° C. Then this solution is carefully added to a solution of 7 (1 g, 3.46 mmol, 1 eq) in dry methanol (90 ml) and the resulting mixture is stirred for 24 h. After 24 h another 0.5 eq of octanethiol and NaBH$_4$ are added in the same way as previously and the mixture is stirred for another 24 h. The solvent is evaporated in vacuo to dryness, the crude is purified over silica gel (cyclohexane/EtOAc 9:1-7:3 as eluent) to afford compound 8 (1.2 g, yield=79.6%) as a pure product.

$^1$H NMR (CDCL$_3$, 400 MHz) δ 5.83 (NH), 4.14 (6H, d, J=2.38 Hz, CH$_2$—C≡CH), 3.83 (6H, s, CH$_2$—O), 2.75 (2H, t, J=7.35 Hz, S—CH$_2$—CH$_2$—C=O), 2.50 (2H, t, J=7.45 Hz, S—CH$_2$—CH$_2$), 2.46-2.35 (5H, m S—CH$_2$—CH$_2$—C=O, CH—C), 1.56 (2H, m, CH$_2$—CH$_2$—S), 1.32 (10H, m, CH$_2$×5), 0.86 (3H, t, J=6.89 Hz CH$_3$—CH$_2$); $^{13}$C NMR (CDCl$_3$, 100 MHz) δ 171.51 (C=O), 79.66 (C≡CH), 74.75 (C≡CH), 68.66 (CH$_2$—O), 59.46 (C), 58.79 (CH$_2$—C≡CH), 37.71 (S—CH$_2$—CH$_2$—C=O), 32.48 (S—CH$_2$—CH$_2$), 31.92 (CH$_2$), 29.75, 29.31, 29.30, 29.01, (CH$_2$×5), 27.77 (S—CH$_2$—CH$_2$—C=O), 22.75 (CH$_2$), 14.56 (CH$_3$).

d) Synthesis of Compound N-(1,3-bis(prop-2-yn-1-yloxy)-2-((prop-2-yn-1-yloxy)methyl)propan-2-yl)-3-(dodecylthio)propanamide (compound 9 R=C$_{10}$H$_{21}$)

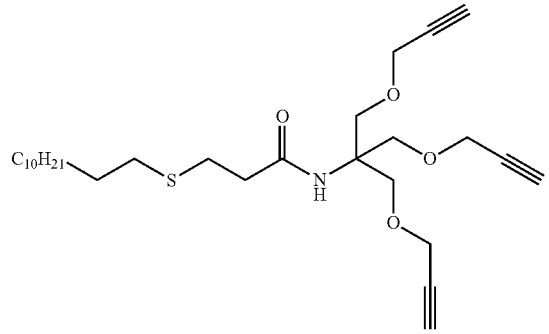

9

Same procedure as compound 8 (see table 1).

$^1$H NMR (CDCL$_3$, 400 MHz) δ5.83 (NH), 4.10 (6H, d, J=2.40 Hz, CH$_2$—C≡CH), 3.79 (6H, s, CH$_2$—O), 2.71 (2H, t, J=7.45 Hz S—CH$_2$—CH$_2$—C=O), 2.46 (2H, t, J=7.55 Hz S—CH$_2$—CH$_2$), 2.42-2.33 (5H, m, S—CH$_2$—CH$_2$—C=O, CH—C), 1.52 (2H, m, CH$_2$—CH$_2$—S), 1.38-1.11 (18H, m, CH$_2$×9), 0.86 (3H, t, J=6.85 Hz CH$_3$—CH$_2$); $^{13}$C NMR (CDCl$_3$, 100 MHz) δ 171.39 (C=O), 79.57 (C≡CH), 74.85 (C≡CH), 68.54 (CH$_2$—O), 59.51 (C), 58.68 (CH$_2$—C≡CH), 37.58 (S—CH$_2$—CH$_2$—C=O), 32.36 (S—CH$_2$—CH$_2$), 31.91 (CH$_2$), 29.65, 29.62, 29.60, 29.54, 29.45, 29.34, 29.26 29.17, 28.91, (CH$_2$×9) 27.66, (S—CH$_2$—CH$_2$—C=O), 22.68 (CH$_2$), 14.12 (CH$_3$). ESI Calcd for C$_{13}$H$_{18}$NO$_3$: 492.31 [M+H$^+$], found m/z 492.31 [M+H$^+$]. HRMS calculated: C$_{28}$H$_{45}$NO$_4$S: 492.3148 [M+H$^+$], found m/z: 492.3148 [M+H$^+$].

e) Synthesis of Compound N-(1,3-bis(prop-2-yn-1-yloxy)-2-((prop-2-yn-1-yloxy)methyl)propan-2-yl)-3-(hexadecylthio)propanamide (compound 10 R=C₁₄H₂₉)

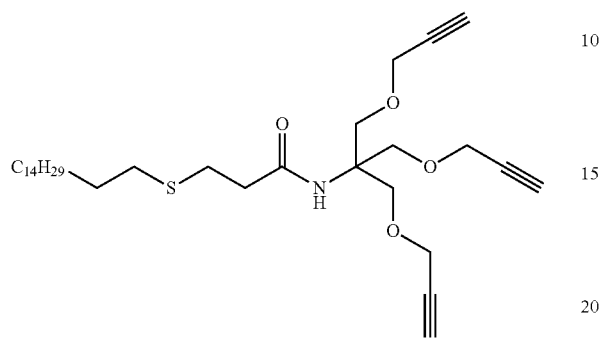

Same procedure as compound 8 (see table 1).

¹H NMR (CDCL₃, 400 MHz) δ 5.84 (NH), 4.14 (6H, d, J=2.37 Hz, CH₂—C≡CH), 3.84 (6H, s, CH₂—O), 2.76 (2H, t, J=7.46 Hz S—CH₂—CH₂—C=O), 2.51 (2H, t, J=7.55 Hz, S—CH₂—CH₂), 2.46-2.39 (5H, m, S—CH₂—CH₂—C=O, CH≡C), 1.56 (2H, m, CH₂—CH₂—S), 1.39-1.14 (26H, m, CH₂×13), 0.87 (3H, t, J=6.84 Hz CH₃—CH₂); ¹³C NMR (CDCl₃, 100 MHz) δ 171.53 (C=O), 79.69 (C≡CH), 74.77 (C≡CH), 68.70 (CH₂—O), 59.49 (C) 58.82 (CH₂—C≡CH), 37.74 (S—CH₂—CH₂—C=O), 32.51 (S—CH₂—CH₂), 32.05 (CH₂), 29.82, 29.79, 29.68, 29.48, 29.40, 29.05, 28.91, (CH₂×13), 27.66, (S—CH₂—CH₂—C=O), 22.81 (CH₂), 14.24 (CH₃). ESI Calcd for $C_{13}H_{18}NO_3$: 548.37 [M+H⁺], found m/z 548.38 [M+H⁺]. HRMS calculated: $C_{28}H_{45}NO_4S$: 548.3776 [M+H⁺], found m/z: 548.3774 [M+H⁺].

TABLE 1

Experimental conditions of Mickaël addition (AB3 building blocks).

| | 9 | 10 |
|---|---|---|
| R—C₂H₄SH | Dodecanethiol | Hexadecanethiol |
| | 0.360 g (1.78.10⁻³ mol) | 0.190 g (7.37 10⁻⁴ mol) |
| NaBH₄ | 0.161 g (4.255.10⁻³ mol) | 0.066 g (1.75 10⁻³ mol) |
| (structure 7) | 0.4103 g (1.74.10⁻³ mol) | 0.200 g (7.0210⁻⁴ mol) |
| Mass of product | 0.749 g | 0.321 g |
| Yield | 88.3% | 83.5% |

1.2. Synthesis of the monocatenar scaffold (via Mickaël addition) with different hydrocarbon chain lengths (AB2 building blocks)

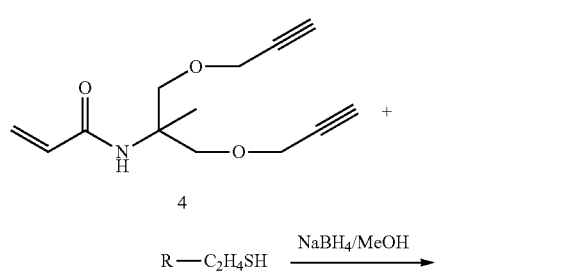

11 R = $C_6H_{13}$
12 R = $C_{10}H_{21}$
13 R = $C_{14}H_{29}$ a) Synthesis of compound N-(2-methyl-1,3-bis(prop-2-yn-1-yloxy)propan-2-yl)-3-(octylthio)propanamide (compound 11)

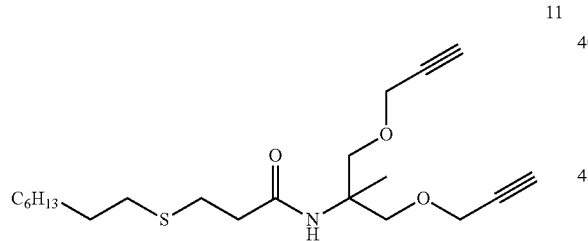

Same procedure as compound 8 (experimental conditions given on table 2).

$^1$H NMR (CDCL$_3$, 400 MHz) δ 5.85 (1H, s, NH), 4.16 (4H, d, J=2.36 Hz CH$_2$—C≡CH), 3.73 (4H, dd, J=9.04, 51.99 Hz CH$_2$—O), 2.71 (2H, t, J=7.41 Hz S—CH$_2$—CH$_2$—C=O), 2.52 (2H, t, J=7.41 Hz CH$_2$—S); 2.41 (2H, t, J=2.37 Hz CH≡C), 2.37 (2H, t, J=7.42 Hz S—CH$_2$—CH$_2$—C=O), 1.56 (2H, m, CH$_2$—CH$_2$—S), δ=1.42-1.19 (13H, m, CH—CH$_2$, CH$_3$—C), 0.87 ppm (3H, t, J=6.89 Hz CH$_3$—CH$_2$); 3C NMR (CDCl$_3$, 100 MHz) δ 171.35 (C=O), 79.72 (C≡CH), 74.77 (C≡CH), 72.19 (CH$_2$—O), 58.79 (CH$_2$—C≡CH), 56.59 (C), 37.87 (S—CH$_2$—CH$_2$—C=O), 32.57 (S—CH$_2$—CH$_2$), 31.96 (CH$_2$), 29.80, 29.35, 29.06, 27.87, (CH$_2$×6), 22.79 (CH$_2$), 19.30, 14.24 (CH$_3$). ESI Calcd for C$_{13}$H$_{18}$NO$_3$: 382.13 [M+H], found m/z 382.24 [M+H]. HRMS calculated: C$_{21}$H$_{35}$NO$_3$S: 382.2417 [M+H$^+$], found m/z: 382.2416 [M+H$^+$].

b) Synthesis of compound N-(2-methyl-1,3-bis(prop-2-yn-1-yloxy)propan-2-yl)-3-(dodecylthio)propanamide (compound 12)

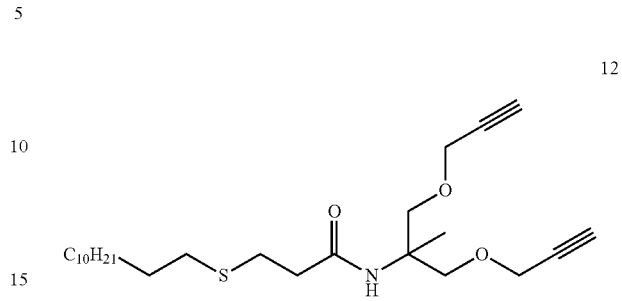

Same procedure as compound 8 (experimental conditions given on table 2).

$^1$H NMR (CDCL$_3$, 400 MHz) δ 5.85 (1H, s, NH), 4.09 (4H, d, J=2.39 Hz CH$_2$—C≡CH), 3.60 (4H, dd, J=9.03, 50.47 Hz CH$_2$—O), 2.70 (2H, t, J=7.40 Hz S—CH$_2$—CH$_2$—C=O), 2.45 (2H, t, J=7.40 Hz CH$_2$—S), 2.40 (2H, t, J=2.40 Hz S—CH$_2$—CH$_2$—C=O), 2.34 (2H, t, J=7.40 Hz CH—C), 1.51 (2H, m, CH$_2$—CH$_2$—S), 1.36-0.94 (21H, m, CH$_3$—CH$_2$, CH$_3$—C), 0.81 ppm (3H, t, J=6.87 Hz CH$_3$—CH$_2$); $^{13}$C NMR (CDCl$_3$, 100 MHz) δ 171.15 (C=O), 79.56 (C≡CH), 74.68 (C≡CH), 71.96 (CH$_2$—O), 58.58 (CH$_2$—C≡CH), 56.40 (C), 37.64 (S—CH$_2$—CH$_2$—C=O), 32.35 (S—CH$_2$—CH$_2$), 31.87 (CH$_2$), 29.61, 29.59, 29.57, 29.51, 29.30, 29.22, 28.87, 27.68, (CH$_2$×10), 22.64 (CH$_2$), 19.14, 14.09 (CH$_3$). ESI Calcd for C$_{13}$H$_{18}$NO$_3$: 438.30 [M+H], found m/z 438.30 [M+H$^+$]. HRMS calculated: C$_{25}$H$_{43}$NO$_3$S: 438.3039 [M+H$^+$], found m/z: 438.3042 [M+H$^+$].

c) Synthesis of compound N-(2-methyl-1,3-bis(prop-2-yn-1-yloxy)propan-2-yl)-3-(hexadecylthio)propanamide (compound 13)

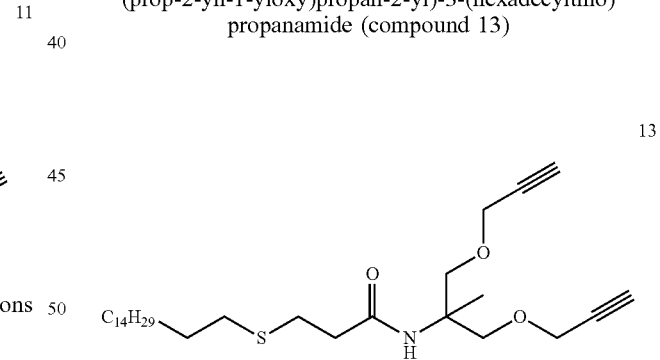

Same procedure as compound 8 (experimental conditions given on table 2).

$^1$H NMR (CDCL$_3$, 400 MHz) δ 5.85 (1H, s, NH), 4.10 (4H, d, J=2.37 Hz CH$_2$—C≡CH); 3.61 (4H, dd, J=9.03, 50.74 Hz CH$_2$—O), 2.71 (2H, t, J=7.40 Hz S—CH$_2$—CH$_2$—C=O), 2.46 (2H, t, J=7.40 Hz CH$_2$—S), 2.40 (2H, t, J=2.37 Hz S—CH$_2$—CH$_2$—C=O), 2.35 (2H, t, J=7.40 Hz CH≡C), 1.52 (2H, m, CH$_2$—CH$_2$—S), 1.38-1.11 (29H, m, CH$_3$—CH$_2$, CH$_3$—C), 0.82 (3H, t, J=6.85 Hz CH$_3$—CH$_2$); $^{13}$C NMR (CDCl$_3$, 100 MHz) δ 171.17 (C=O), 79.59 (C≡CH), 74.69 (C≡CH), 72.01 (CH$_2$—O), 58.62 (CH2-C≡CH), 56.44 (C), 37.69 (S—CH$_2$—CH$_2$—C=O), 32.39 (S—CH$_2$—CH$_2$), 31.92 (CH$_2$), 29.69, 29.66, 29.61, 29.55, 29.36, 29.26, 28.91, 27.72, (CH$_2$×10), 22.69, (CH$_2$), 19.17, 14.12 (CH$_3$). ESI Calcd for C$_{13}$H$_{18}$NO$_3$: 494.36 [M+H], found m/z 494.37 [M+H$^+$]. HRMS calculated: C$_{29}$H$_{51}$NO$_3$S: 494.3666 [M+H$^+$], found m/z: 494.3668 [M+H$^+$].

TABLE 2

Experimental conditions of Mickaël addition (AB2 building blocks).

| | 11 | 12 | 13 |
|---|---|---|---|
| R—C$_2$H$_4$SH | Octanethiol 0.269 g (1.84.10$^{-3}$ mol) | Dodecanethiol 0.269 g (1.84.10$^{-3}$ mol) | Hexadecanethiol 0.231 g (8.9.10$^{-4}$ mol) |
| NaBH$_4$ | 0.165 g (4.37.10$^{-3}$ mol) | 0.1598 g (4.22.10$^{-3}$ mol) | 0.0804 g (2.13.10$^{-3}$ mol) |
| 4 | 0.412 g (1.75.10$^{-3}$ mol) | 0.412 g (1.75.10$^{-3}$ mol) | 0.200 g (8.5.10$^{-4}$ mol) |
| Mass of Product | 0.450 g | 0.237 g | 0.280 g |
| Yield | 67.44% | 45.20% | 66.71% |

1.3. Functionalization with hydrophilic PolyTris moieties a) Synthesis of Hydrocarbon dendriTAC H8G$_0$triTAC (5*3) (Compound 14)

Sodium ascorbate (57 mg, 0.286 mmol, 1.1 eq), compound 11 (112 mg, 0.26 mmol, 1 eq) and azido-polyTRIS oligomer 2b (DPn~5) (1.006 g, 1.01 mmol, 3.9 eq) are dissolved in mixture of DMF (7 ml) and water (4 ml), the reaction mixture is heated to 55° C., and after 5 minutes copper sulfate pentahydrate (17 mg, 0.068 mmol, 0.26 eq) is added. The solution is stirred at 60° C. during 3 hours and then at room temperature overnight. The solution is filtered and passed through chelex beads, and then the solvent is carefully removed under high vacuum. The crude is dissolved in a mixture of MeOH/water 9/1 and filtered and then purified over LH20 MeOH/Water 9/1. The purification is followed by TLC (Ethyl Acetate/MeOH 5/5) only fraction where only compounds staying at the start were recovered.

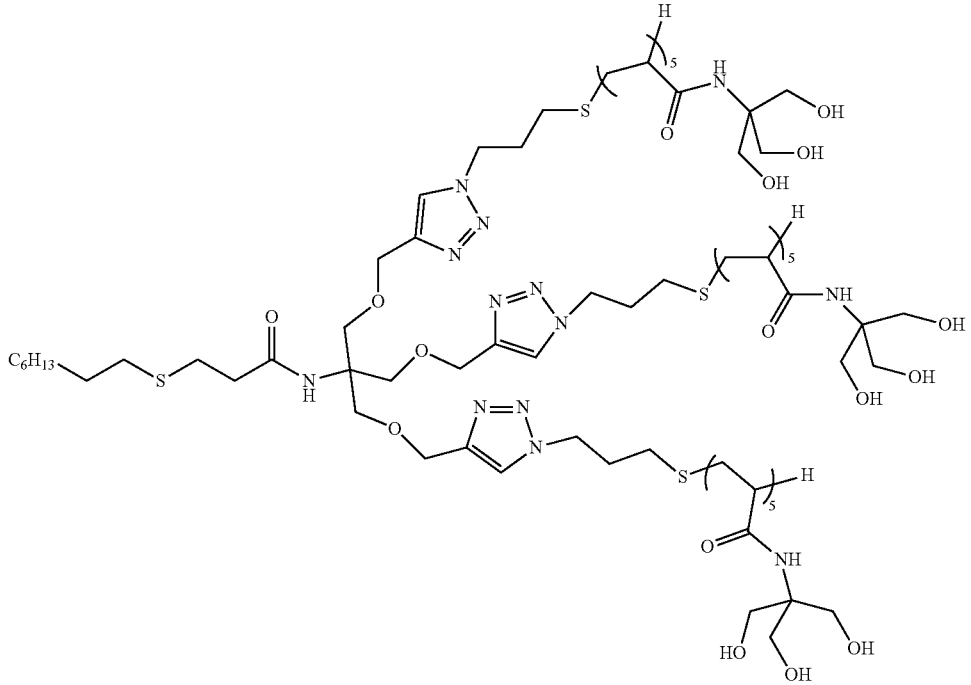

14

The solvent is carefully removed in vacuo at a temperature around 0° C. at the beginning and then at room temperature without the water bath, diluted with water and freeze dried to obtain 377 mg of compound 14 as a white powder (yield=43.03%).

$^1$H NMR (DMSO-d6, 400 MHz) δ 8.05 (3H, s, CH triazole), 7.71-6.79 (16H, c, NH), 5.39-4.56 (48H, c, OH), 4.47 (6H, s, C$_{TRIAZOLE}$—CH$_2$—O), 4.40 (6H, s, CH$_2$—CH$_2$—N$_{TRIAZOLE}$), 3.86-3.42 (133H, br, CH$_2$—OH, CH$_2$—O—), 2.68 (4H, c, CH$_2$—CH$_2$—S, S—CH$_2$—CH$_2$—C=O), 2.37-1.86 (27H, c, CH$_2$—CH$_2$—CH$_2$—S, CH$_2$—S, CH, CH$_2$—C=O, 1Ha —CH$_2$—CH$_2$—C=O CH—C=OLIGOMER), 1.82-1.09 (42H, c, CH$_{2alkyl\ chain}$ CH$_{2\ OLIGOMER}$), 0.85 (3H, t, J=6.95 Hz CH$_3$).

b) Synthesis of Hydrocarbon dendriTAC H12G$_0$triTAC (5*3) (Compound 15)

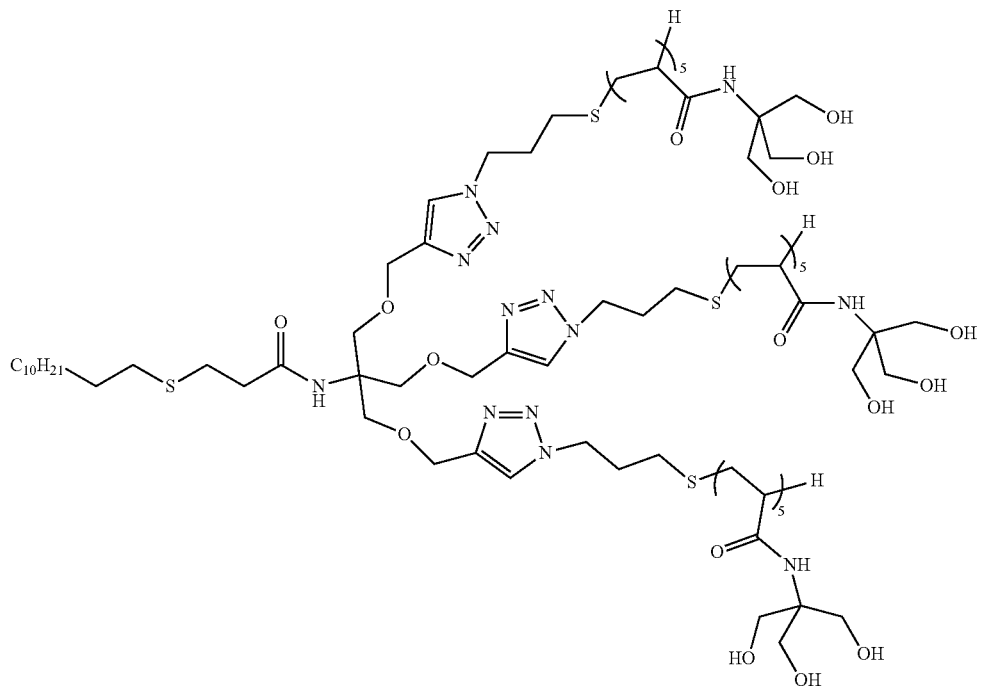

Same procedure as compound 14 (see experimental conditions on table 3).

$^1$H NMR (DMSO-d6, 400 MHz) δ 8.04 (3H, s, CH triazole), 7.78-6.69 (25H, c, NH), 5.43-4.57 (75H, c, OH), 4.48 (6H, d, J=7.31 Hz C$_{TRIAZOLE}$—CH$_2$—O), 4.40 (6H, s, CH$_2$—CH$_2$—N$_{TRIAZOLE}$), 3.86-3.37 (150H, br, CH$_2$—OH, CH$_2$—O—), 2.72 (4H, c, CH$_2$—CH$_2$—S, S—CH$_2$—CH$_2$—C=O), 2.29-1.84 (40H, c, CH$_2$—CH$_2$—CH$_2$—S, CH$_2$—S, CH, CH$_2$—C=O, 1Ha —CH$_2$—CH$_2$—C=O CH—C=O$_{OLIGOMER}$), 1.79-1.13 (75H, c, CH$_{2alkyl\ chain}$ CH$_{2\ OLIGOMER}$), 0.85 (3H, t, J=6.63 Hz CH$_3$).

c) Synthesis of Hydrocarbon dendriTAC H16G₀triTAC (5*3) (Compound 16)

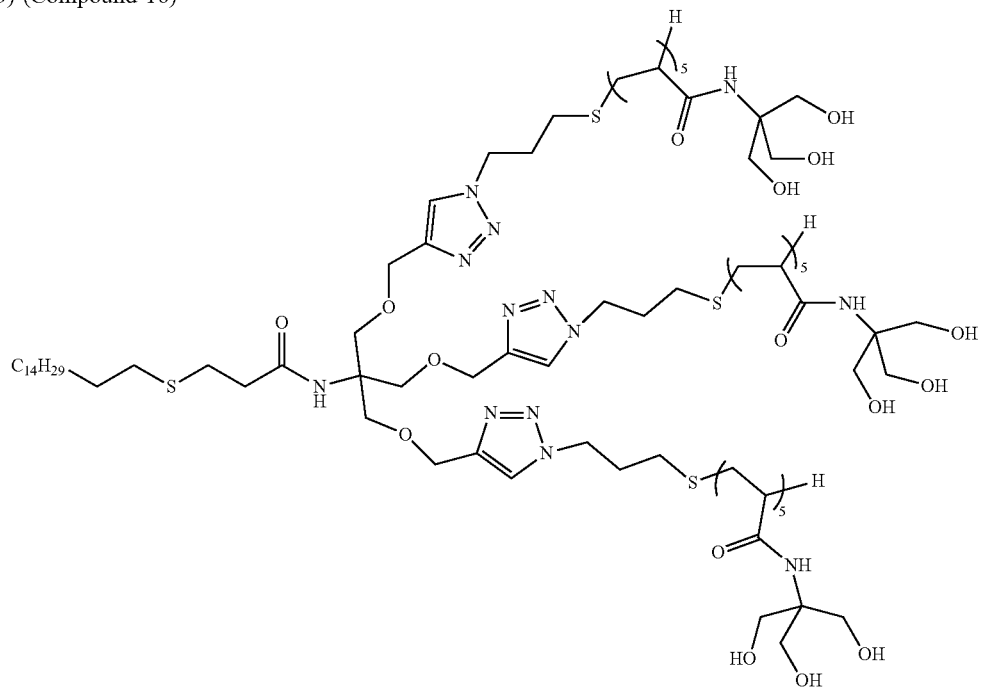

16

Same procedure as compound 14 (see experimental conditions on table 3).

¹H NMR (DMSO-d6, 400 MHz) δ 8.03 (3H, s, CH triazole), 7.74-6.75 (19H, c, NH), 5.50-4.56 (50H, c, OH), 4.47 (6H, d, J=7.64 Hz O$_{TRIAZOLE}$—CH$_2$—O), 4.39 (6H, s, CH$_2$—CH$_2$—N$_{TRIAZOLE}$), 3.91-3.41 (96H, br, CH$_2$—OH, CH$_2$—O—), 2.68 (4H, c, CH$_2$—CH$_2$—S, S—CH$_2$—CH$_2$—C=O), 2.32-1.83 (24H, c, CH$_2$—CH$_2$—CH$_2$—S, CH$_2$—S, CH, CH$_2$—C=O, 1Ha —CH$_2$—CH$_2$—C=O CH—C=O$_{OLIGOMER}$), 1.80-1.01 (50H, c, CH$_{2\,alkyl\,chain}$ CH$_{2\,OLIGOMER}$), 0.85 (3H, t, J=6.73 Hz CH$_3$).

d) Synthesis of Hydrocarbon dendriTAC H8G₀diTAC (5*2) (Compound 17)

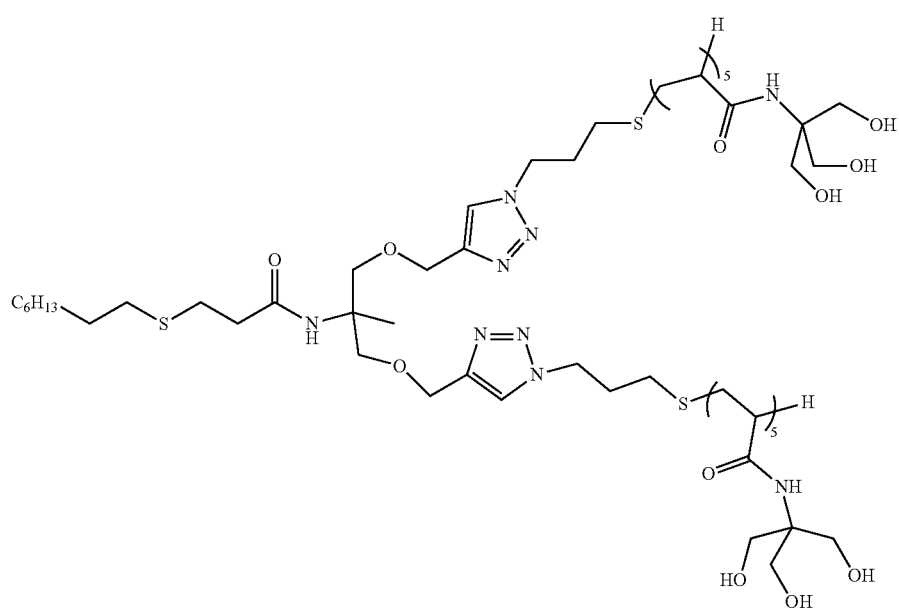

17

Same procedure as compound 14 (see experimental conditions on table 3); equivalents number of oligomer 2b is 2.6 instead of 3.9.

$^1$H NMR (DMSO-d6, 400 MHz) δ 8.04 (2H, s, CH triazole), 7.74-6.75 (19H, c, NH), 5.57-4.58 (54H, c, OH), 4.49 (4H, $C_{TRIAZOLE}$—CH$_2$—O), 4.40 (4H, s, CH$_2$—CH$_2$—N$_{TRIAZOLE}$), 3.97-3.43 (110H, br, CH$_2$—OH, CH$_2$—O—), 2.57 (3H, m, Ha CH$_2$—CH$_2$—S oligomer S—CH$_2$—CH$_2$—C=O), 2.45 (3H, m, Hb CH$_2$—CH$_2$—S oligomer CH$_2$—CH$_2$—S), 2.29 (2H, m, S—CH$_2$—CH$_2$—C=O), 2.27-1.85 (27H, c, CH$_2$—CH$_2$—CH$_2$—S, CH$_2$—S, CH, CH$_2$—C=O, 1Ha —CH$_2$—CH$_2$—C=O CH—C=O$_{OLIGOMER}$), 1.76-1.09 (50H, c, CH$_{2\,alkyl\,chain}$ CH$_{2\,OLIGOMER}$), 0.85 (3H, t, J=6.80 Hz CH$_3$).

e) Synthesis of Hydrocarbon dendriTAC H12G$_0$diTAC (5*2) (Compound 18)

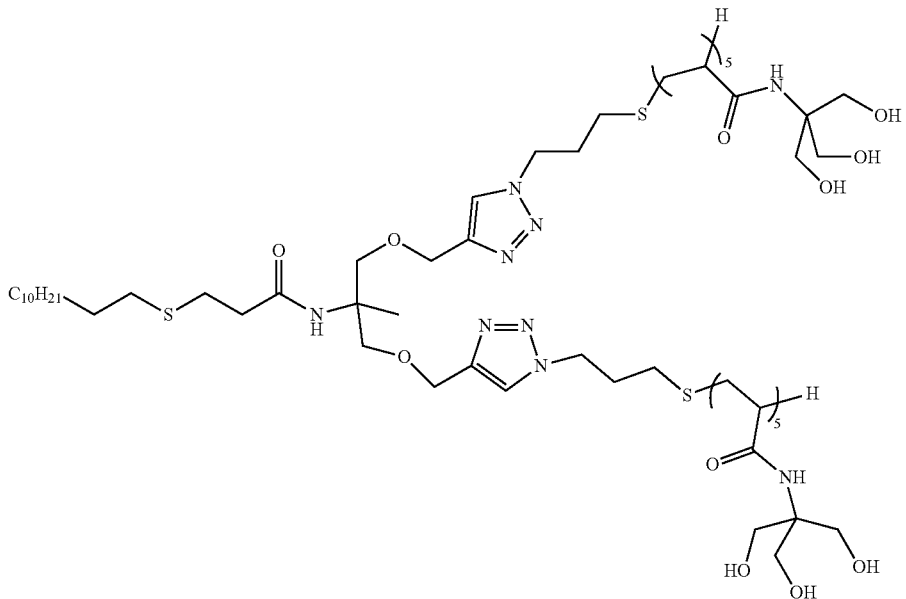

Same procedure as compound 14 (see experimental conditions on table 3); equivalents number of oligomer 2b is 2.6 instead of 3.9.

$^1$H NMR (DMSO-d6, 400 MHz) δ 8.05 (2H, s, CH triazole), 7.77-6.72 (21H, c, NH), 5.30-4.56 (53H, c, OH), 4.49 (4H, $C_{TRIAZOLE}$—CH$_2$—O), 4.40 (4H, s, CH$_2$—CH$_2$—N$_{TRIAZOLE}$), 3.95-3.41 (104H, br, CH$_2$—OH, CH$_2$—O—), 2.57 (3H, m, Hb CH$_2$—CH$_2$—S oligomer S—CH$_2$—CH$_2$—C=O), 2.45 (3H, m, Hb CH$_2$—CH$_2$—S oligomer CH$_2$—CH$_2$—S), 2.31 (2H, m, S—CH$_2$—CH$_2$—C=O), 2.26-1.82 (27H, c, CH$_2$—CH$_2$—CH$_2$—S, CH$_2$—S, CH, CH$_2$—C=O, 1Ha —CH$_2$—CH$_2$—C=O CH—C=O$_{OLIGOMER}$), 1.77-1.11 (50H, c, CH$_{2\,alkyl\,chain}$ CH$_{2\,OLIGOMER}$), 0.85 (3H, t, J=6.75 Hz CH$_3$).

f) Synthesis of Hydrocarbon dendriTAC H16G₀diTAC (5*2) (Compound 19)

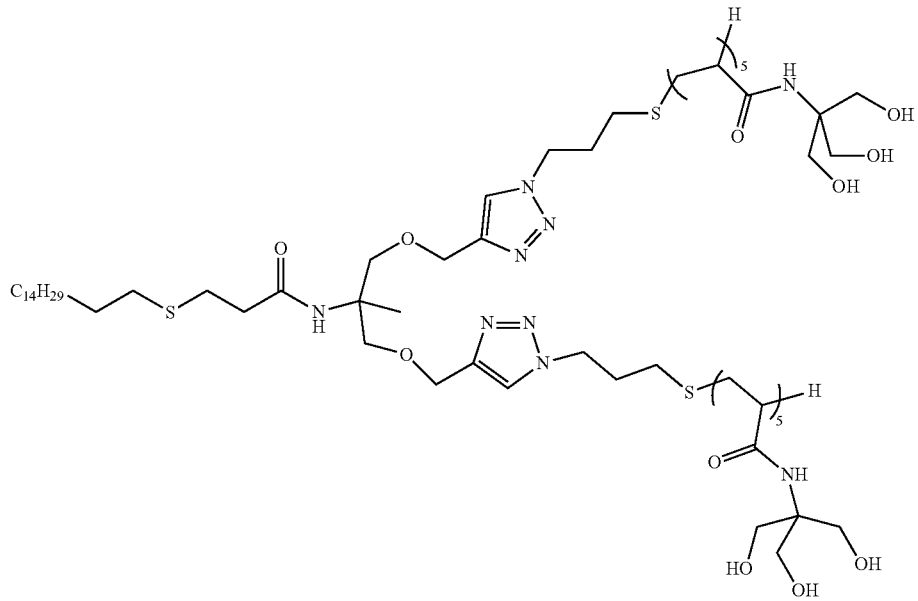

19

Same procedure as compound 14 (see experimental conditions on table 3); equivalents number of oligomer 2b is 2.6 instead of 3.9.

$^1$H NMR (DMSO-d6, 400 MHz) δ 8.04 (2H, s, CH triazole), 7.79-6.56 (18H, c, NH), 5.45-4.57 (50H, c, OH), 4.48 (4H, d, J=7.52 Hz $C_{TRIAZOLE}$—$CH_2$—O), 4.40 (4H, s, $CH_2$—$CH_2$—$N_{TRIAZOLE}$), 3.93-3.41 (100H, br, $CH_2$—OH, $CH_2$—O—), 2.29-1.84 (25H, c, $CH_2$—$CH_2$—$CH_2$—S, $CH_2$—S, CH, $CH_2$—C=O, 1Ha —$CH_2$—$CH_2$—C=O CH—C=$O_{OLIGOMER}$), 1.79-1.03 (50H, c, $CH_{2 alkyl\ chain}$ $CH_2\ _{OLIGOMER}$), 0.85 (3H, t, J=6.70 Hz $CH_3$).

TABLE 3

Experimental conditions for the cycloaddition step.

| Final surfactant | 14 | 15 | 16 | 17 | 18 | 19 |
|---|---|---|---|---|---|---|
| Propargyl compound | 11 | 12 | 13 | 8 | 9 | 10 |
| mass | 0.112 g | 0.075 g | 0.054 g | 0.150 g | 0.146 g | 0.150 g |
| mol | $2.57 \cdot 10^{-4}$ | $1.5 \cdot 10^{-4}$ | $9.87 \cdot 10^{-5}$ | $3.39 \cdot 10^{-4}$ | $3.34 \cdot 10^{-4}$ | $3.04 \cdot 10^{-4}$ |
| Oligomer 2b | 1.006 g | 0.775 g | 0.518 g | 1.059 g | 0.929 g | 1.631 g |
|  | ($1.01 \cdot 10^{-3}$ mol) | ($7.07 \cdot 10^{-4}$ mol) | ($3.85 \cdot 10^{-4}$ mol) | ($10.21 \cdot 10^{-4}$ mol) | ($8.85 \cdot 10^{-4}$ mol) | ($7.9 \cdot 10^{-4}$ mol) |
| Copper (II) sulfate | 17 mg | 17 mg | 6 mg | 32 mg | 23 mg | 20 mg |
|  | ($0.07 \cdot 10^{-4}$ mol) | ($6.81 \cdot 10^{-5}$ mol) | ($2.57 \cdot 10^{-5}$ mol) | ($1.02 \cdot 10^{-4}$ mol) | ($8.82 \cdot 10^{-5}$ mol) | ($7.9 \cdot 10^{-5}$ mol) |
| Sodium ascorbate | 57 mg | 49 mg | 215 mg | 85 mg | 71 mg | 66 mg |
|  | ($2.86 \cdot 10^{-4}$ mol) | ($2.47 \cdot 10^{-4}$ mol) | ($1.08 \cdot 10^{-4}$ mol) | ($4.32 \cdot 10^{-4}$ mol) | ($3.7 \cdot 10^{-4}$ mol) | ($7.9 \cdot 10^{-5}$ mol) |
| Mass of product | 0.377 g | 0.212 g | 0.130 g | 0.236 g | 0.499 g | 0.162 g |
| Yield | 43.03% | 40.69% | 28.80% | 29.99% | 62.87% | 21.74% |

Example 3: Synthesis of the F- or H-TAC Telomers

The synthesis of F- and H-TAC telomers (Scheme 3) was already reported by Pucci et al. (*European Polymer Journal.* 1991, 27, 1101-1106; *Curr. Med. Chem. Anticancer Agents.* 2 (2002) 645-665).

Scheme 3: General structure and nomenclature of H-TAC and F-TAC

General structure of H-TAC and F-TAC telomers:

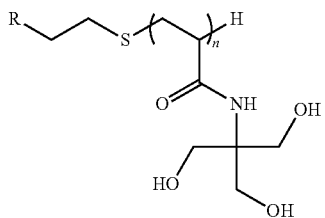

H-TAC: R = CxH$_{2x+1}$
F-TAC: R = CxF$_{2x+1}$

Nomenclature:

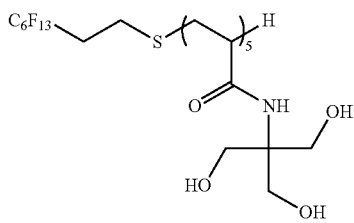

R = C$_6$F$_{13}$
n = 5

F6TAC5 means R = C6F13 and n = 5

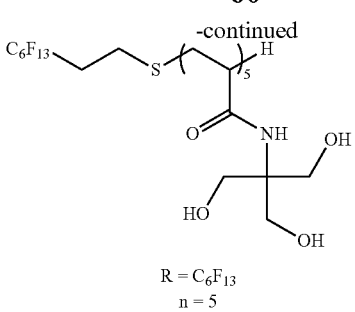

R = C$_6$F$_{13}$
n = 5

H8TAC5 means R = C6H13 and n = 5

F- or H-TAC telomers are obtained by free radical telomerization of an acryloyl monomer derived from Tris, the tris(hydroxymethyl)acrylamidomethane (THAM), or from its peracetylated analogue (tris(acetoxymethyl)acrylamidomethane), in the presence of an alkane (for H-TAC) or a fluoroalkanethiol (for F-TAC) as a transfer reagent called "telogen". The synthesis of the two polymerizable monomers THAM or peracetylated THAM analogue is performed as previously reported (Jasseron et al. *European Journal of Medicinal Chemistry* 2003, 38, 825-836; Astafyeva et al. *J. Mater. Chem. B* 2015, 3, 2892-2907). The physico-chemical parameters of the resulting telomers (molecular weight, Hydrophilic Lipophilic Balance, electric charge) can be adjusted through both the starting material and the experimental conditions (Pucci et al., ibid.). Telomerization experiments are respectively performed in methanol (MeOH), when the monomer THAM is used as starting material, and in tetrahydrofuran (THF) for peracetylated THAM. The use of this later monomer is necessary for the synthesis of telomers with a degree of polymerization (DPn; average number of repeating units on the polymeric backbone+1 (telogen moiety)) higher than 15 due to the limited solubility of polyTris oligomers in pure methanol for such DPn values (Giusti et al., *New J. Chem.* 2002, 26, 1724-1732). Alternatively, it is also possible to synthetise telomers with a DPn higher than 15 starting from THAM using a mixture of MeOH/H2O (90/10 to 80/20, v/v) as solvent.

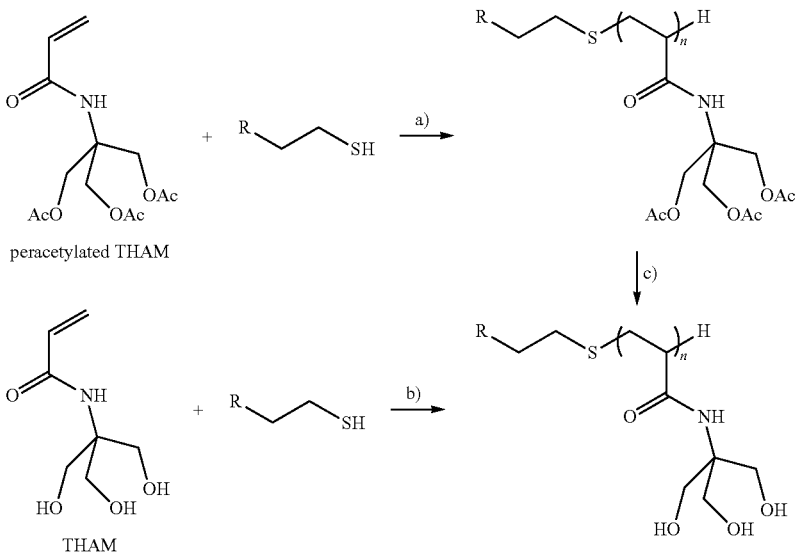

Synthesis of F- and H-TAC Surfactants.

Reagents and conditions: (a) AIBN/THF, reflux (62-66%); (b) i: AIBN/CH$_3$OH, reflux or ii: AIBN/[CH$_3$OH/H2O, 90/10, v/v], reflux (62-73%); (c) MeONa cat./MeOH, room temperature (100%).

Telomerization experiments are carried out by refluxing monomer THAM or peracetylated THAM in dry and degassed appropriate solvent, under a nitrogen atmosphere, in the presence of alkane- or fluoroalkanethiol as transfer reagent and AIBN (a,a'-azobisisobutyronitrile) as radical initiator. The AIBN concentration in the reaction mixture is ten times lower than the telogen one (C. M. Starks, Free radical telomerization, Academic Press, New York, 1974). The starting proportions of monomer THAM or peracetylated THAM and telogen used are reported in table 4. These proportions are chosen taking into account previous results obtained with THAM telomerization. The reaction is monitored by thin layer chromatography and pursued until complete disappearance of each monomer (4 to 12 h). For telomers prepared starting from THAM, the solution is then concentrated and subsequently precipitated in diethyloxyde. The precipitate is dissolved in water and freeze dried to give final surfactants as white powders. As regards peracetylated telomers, after total disappearance of monomer peracetylated THAM, a final treatment under Zemplén conditions (Astafyeva et al., ibid.) provides the desired water soluble telomers in satisfactory yields and NMR analysis confirms the total disappearance of acetyl groups. Telomers with DPn>15 are all purified by precipitation in diethyloxyde. The resulting precipitate is dissolved in water and a dialysis (cut off of 1000) is performed overnight, the solution is freeze dried to obtain final surfactants as white powders.

For all the series of telomers, the degree of polymerization depends on the telogen/monomer ratio adjusted through both starting materials and experimental conditions (Pucci et al. *European Polymer Journal* 1988, 24, 1077-1086). For a given transfer reagent, it may vary from one (monoadduct) to several tens. DPn are determined in 1H-NMR or 19F-NMR by comparing the area of typical signals ascribed to each monomer and telogen.

For example, in the case of hydrocarbon telomers (H-TAC) DPn values are determined by comparing peaks area assigned to the terminal methyl signal in the hydrocarbon tail (d 0.9 ppm, integral 3H) respectively to hydroxyl groups of THAM (d 4.5-5.3 ppm, integral 3 nH) or to methylene protons of peracetylated THAM (d 4.32 ppm, integral 6nH). Concerning fluorocarbon telomers (F-TAC) the DPn is assessed by quantification of fluorine using 19F-NMR as described by Astafyeva et al. (ibid.).

TABLE 4

Conditions of F- or H-TAC synthesis

| Compound | R | Monomer | Initial Condition [monomer]/[telogen] | solvent | DPn | Yield (%) |
|---|---|---|---|---|---|---|
| F$_6$TAC$_7$ | C$_6$F$_{13}$ | THAM | 3 | MeOH | 7 | 62.2 |
| F$_6$TAC$_{13}$ | C$_6$F$_{13}$ | THAM | 5 | MeOH | 13 | 58.2 |
| F$_6$TAC$_{18}$ | C$_6$F$_{13}$ | THAM(OAc) | 15 | THF | 18 | 46.6 |
| F$_6$TAC$_{22}$ | C$_6$F$_{13}$ | THAM(OAc) | 20 | THF | 22 | 55.7 |
| H$_8$TAC$_6$ | C$_6$H$_{13}$ | THAM(OAc) | 5 | THF | 6 | 56.4 |
| H$_8$TAC$_8$ | C$_6$H$_{13}$ | THAM | 5 | MeOH | 8 | 50.5 |
| H$_8$TAC$_9$ | C$_6$H$_{13}$ | THAM | 6 | MeOH | 9 | 49 |
| H$_{12}$TAC$_6$ | C$_{10}$F$_{21}$ | THAM | 6 | MeOH | 6 | 38.8 |
| H$_{12}$TAC$_9$ | C$_{10}$F$_{21}$ | THAM | 8 | MeOH | 9 | 44.8 |

Example 4: Study of the Phases Separation

An equal volume of organic solvent and aqueous (water+amhiphile) phases were contacted and shaken for 5 min at 20° C. The mixture was let to separate for 5 mins, and phase separation was visually characterized. In the case of the presence of an emulsion, the mixture was centrifuged at 5000 rpm for 3 min, then visually observed again. When persisting in this case, the emulsion was qualified as "stable".

| Solvent | toluene | toluene | toluene | toluene | toluene | toluene |
|---|---|---|---|---|---|---|
| Amphiphile (amount) | Sodium dodecyl sulfate (SDS) (2% wt) | TPGS-750M (2% wt) | H8-TAC6 (2% wt) | F6-TAC6 (2% wt) | Zonyl UR (2% wt) | Brij 35 (2% wt) |
| Result | Stable Emulsion | Stable Emulsion | Clean phase separation | Clean phase separation | Stable Emulsion | Stable Emulsion |

Zonyl UR is a fluorinated phosphate (mixture of mono & di esters, DuPont product), Brij 35 is a non-ionic surfactant (C12-(EO)23).

The surfactants of the invention enable clean phase separation, whereas the surfactants SDS, TPGS-750M, Zonyl UR and Brij 35 lead to a stable emulsion.

Example 5: Study of the Phases Separation in Presence of an Extractant

An equal volume of organic (extractant+diluent) and aqueous (water+amhiphile) phases were contacted and shaken for 5 min at 20° C. The mixture was let to separate for 5 mins, and phase separation was visually characterized. In the case of the presence of an emulsion, the mixture was centrifuged at 5000 rpm for 3 min, then visually observed again. When persisting in this case, the emulsion was qualified as "stable".

| Diluent | toluene | toluene | toluene | toluene | toluene | toluene | none |
|---|---|---|---|---|---|---|---|
| Extractant (amount) | DMDBTDMA | DMDBTDMA | DMDBTDMA | DMDBTDMA | DMDBTDMA | BESO (0.3 | TBP (pure) |

| Amphiphile (amount) | H8TAC6 (0.5 mol/L) (2% wt) | F6TAC6 (0.5 mol/L) (2% wt) | H16G₀triTAC (0.5 mol/L) (5 * 3) (2% wt) | H12G₀diTAC (0.5 mol/L) (5 * 2) (1% wt) | F6TAC17 (0.5 mol/L) (2% wt) | F6TAC17 (mol/L) (2% wt) | F6TAC17 (2% wt) |
|---|---|---|---|---|---|---|---|
| Result | Clean phase separation | Clean phase separation | Clean phase separation | Clean phase separation | Clean phase separation | Clean phase separation | Clean phase separation |

DMDBTDMA = dimethyldibutyltetradecylmalonamide, BESO = Bis-ethylhexyl sulfoxide, TBP = tributylphosphate.

The surfactants of the invention enable clean phase separation.

Example 6: Extraction of an Organic Phase Comprising Pd Using the Surfactants of the Invention An organic phase loaded with Pd was prepared by contacting a solvent (see table below) with an aqueous solution of nitric acid containing Pd(II) nitrate, followed by shaking for 1 h, and phase separation. The so obtained organic phase (800 µL) was contacted with an aqueous phase (400 µL, see table below), and the system was shaken in a closed cap vial for 30 min at 20° C. The phases were allowed to separate for 5 min, then 200 µL of each phase were taken for quantitative Pd analysis (performed with a SpectroArcos ICP-AES spectrometer). The back extraction yield was determined as follows: yield=amount of Pd in final aqueous phase/amount of Pd in initial organic phase. Quantitative recovery of Pd (within the analytical limits) was checked in all cases (amount of Pd in initial organic phase=amount of Pd in final aqueous phase+amount of Pd in final organic phase).

| Diluent | toluene | toluene | none |
|---|---|---|---|
| Extractant | DMDBTDMA | BESO | TBP |
| (amount) | (0.5 mol/L) | (0.3 mol/L) | (pure) |
| Pd-back extraction yield with water alone | 50% | 2.50% | 13% |
| Pd-back extraction yield with F6-TAC17 (2% wt) | 72% | 31% | 78% |

Example 7: Buchwald-Hartwig Cross-Coupling Reaction Using Commercial Palladium Source in Presence of the Surfactants of the Invention, Compared to TPGS-750M General Procedure (Wagner et al., *Green Chemistry* 16:4170-4178)

Amine (1.2 equiv.) and aryl halide (1 equiv.) were added to an aqueous solution of surfactant (2 wt %, 1 mL/mmol). The mixture was degassed by bubbling Argon, and NaOt-Bu (1.5 equiv.), [(cinnamyl)PdCl]$_2$ (1.1 mol %) and t-BuXPhos (4.4 mol %) were added. The mixture was stirred (at 1200 rpm) at 50° C. (2-24 h). Volatiles were evaporated and the crude residue was purified by chromatography on silica gel.

N-(3-Methylphenyl)-4-methoxybenzamide

Following the general procedure of the Buchwald-Hartwig cross-coupling reaction, we used [(cinnamyl)PdCl]$_2$ (5.7 mg, 0.011 mmol), t-BuXPhos (18.7 mg, 0.044 mmol), 3-bromotoluene (121 µL, 1.0 mmol), p-methoxybenzamide (181 mg, 1.2 mmol) and NaOt-Bu (144 mg, 1.5 mmol) in presence of various surfactants (20 mg in 1 mL of water). Purification was performed by column chromatography on silica gel with the following eluent:n-heptane/ethyl acetate (7/3 to 5/5). After evaporation, N-(3-Methylphenyl)-4-methoxybenzamide was recovered as white solid. 1H NMR (400 MHz, CDCl3) δ 2.34 (s, 3H), 3.87 (s, 3H), 6.95-6.97 (m, 3H), 7.25 (t, J=7.7 Hz, 1H), 7.41 (d, J=7.7 Hz, 1H), 7.51 (s, 1H), 7.80 (d, J=8.9 Hz, 2H), 7.87 (br s, 1H); 13C NMR (101 MHz, CDCl3) δ 21.5, 55.4, 113.9, 117.2, 120.8, 125.1, 127.2, 128.8, 128.9, 138.0, 138.9, 162.4, 165.2.

Results are shown in the table below:

| Surfactant (2%) | Yield (%) | Surfactant (2%) | Yield (%) |
|---|---|---|---|
| TPGS-750-M | 93 | | |
| | | F6TAC7 | 81 |
| F6 G₀diTAC (10*2) | 79 | F6TAC13 | 82 |
| H8G₀triTAC (5*3) | 88 | F6TAC17 | 78 |
| H8G₀diTAC (5*2) | 88 | H8TAC6 | 89 |
| H12G₀diTAC (5*2) | 86 | H8TAC8 | 84 |
| H12G₀triTAC (5*3) | 85 | H8TAC9 | 86 |
| H16G₀triTAC (5*3) | 86 | H12TAC6 | 84 |
| H16G₀diTAC (5*2) | 89 | H12TAC9 | 84 |

Example 8: Suzuki-Miyaura Cross-Coupling Reaction Using Back-Extracted Palladium in Micellar Medium To a solution of back-extracted palladium in water (80 µL) containing the surfactant H12G₀diTAC (5*2) (2% w:w) were added 3-bromoanisole (1 eq., 12.5 mg, 0.00848 mL, 0.0667 mmol), phenylboronic acid (1.2 eq., 9.75 mg, 0.08 mmol), Bippyphos (4.4%, 3.83 mg, 0.00733 mmol) and triethylamine (1.86 eq., 12.5 mg, 0.0172 mL, 0.124 mmol). The reaction mixture was stirred at room temperature for 16 h in a Bioshake IQ at 1 800 rpm. The aqueous phase was extracted with ethyl acetate. This organic phase was evaporated and the crude residue was purified by chromatography on silica gel using ethyl acetate and n-heptane as eluent to provide 1-methoxy-3-phenylbenzene (10.4 mg, 0.057 mmol, 34% yield). 1H NMR (400 MHz, CDCl3): δ 7.58 (d, J=5.2 Hz, 2H), 7.44 (t, J=5.1 Hz, 2H), 7.37-7.34 (m, 2H), 7.18 (d, J=5.1 Hz, 1H), 7.13 (s, 1H), 6.91-6.89 (m, 1H), 3.87 (s, 3H).

The invention claimed is:

1. A process of extraction of at least one metal chosen from the platinum group metals and gold from a first organic liquid composition comprising:
   at least one metal chosen from the platinum group metals and gold, and
   an organic solvent, said organic solvent being water immiscible, wherein said process comprises the following steps:
  a) contacting said first organic liquid composition with a first aqueous solution comprising a surfactant to obtain after phase separation,
    a second aqueous solution comprising the at least one metal chosen from the platinum group metals and gold and the surfactant, and
    a second organic liquid composition comprising the organic solvent;
  b) recovering of said second aqueous solution,
said surfactant comprising:
  an hydrophobic central core of valence m equal to 1, 2 or 3;
when m=1, a hydrophilic group G of the following formula, attached to the central core:

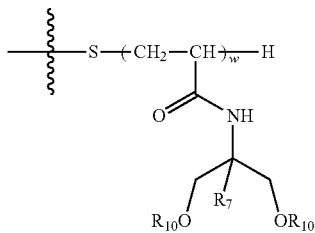

wherein:
$R_7$ is selected from H, $C_1$-$C_6$ alkyl and $CH_2OR_{10}$;
$R_{10}$ is H or a monosaccharide selected from glucose, galactose, mannose;
w is an integer from 1 to 30;
  when m=2 or 3, the surfactant being then a dendrimer of generation n,
    generation chains attached to the central core and branching around the core; and
    an hydrophilic terminal group at the end of each generation chain;
  wherein
  n is an integer from 0 to 12;
  the hydrophilic terminal group comprises:
    a mono-, oligo- or polysaccharide residue,
    a cyclodextrin residue,
    a polyethylene glycol (PEG) residue,
    a peptide residue,
    a tris(hydroxymethyl)aminoethane (Tris), or
    a 2-amino-2-methylpropane-1,3-diol;
  the central core being:
  when m=1, a group,
  wherein:
  W' is $R_F$ or a group selected from W'1, W'2 or W'3:

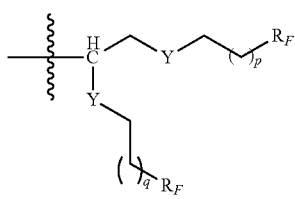

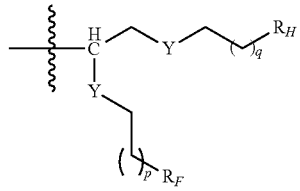

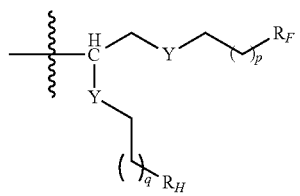

$R_F$ is a $C_4$-$C_{10}$ perfluoroalkyl or a $C_1$-$C_{24}$ alkyl group,
RH is a $C_1$-$C_{24}$ alkyl group,
p is 0, 1, 2, 3 or 4;
q is 0, 1, 2, 3 or 4;
L' is a linear or branched $C_1$-$C_{12}$ alkylene group, optionally interrupted by one or more groups Y';
Y' at each occurrence is chosen from —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH—, O— or —S—,
Y at each occurrence is chosen from —S—, —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH— or —O—;
  when m=2 or 3, a group of formula (Ia) or (Ib):

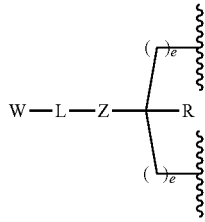

(Ia)

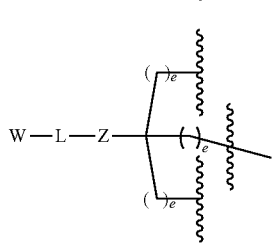

(Ib)

wherein:
W is $R_F$ or a group selected from $W_0$, $W_1$, $W_2$ or $W_3$:

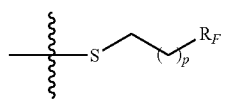

$W_0$

-continued

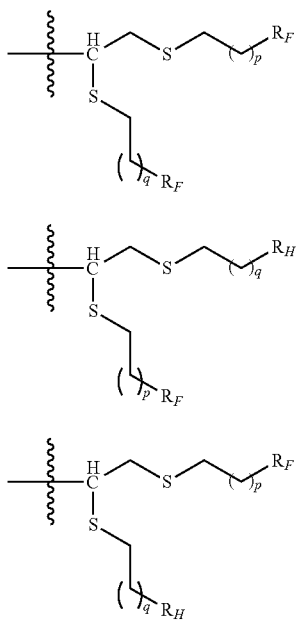

$R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L is a linear or branched $C_1$-$C_{12}$ alkylene group, optionally interrupted by one or more —O—, —S—,
Z is C(=O)NH or NHC(=O),
R is a $C_1$-$C_6$ alkyl group, and
e is at each occurrence independently selected from 0, 1, 2, 3 or 4.

2. The process according to claim 1, wherein said first organic liquid composition results from the liquid/liquid extraction of an original acidic aqueous phase comprising at least one metal chosen from the platinum group metals and gold, with said organic solvent.

3. The process according to claim 1, wherein the organic solvent comprises or consists of an extractant of the at least one metal chosen from the platinum group metals and gold from an acidic aqueous solution and optionally, an organic diluent and/or a phase modifier.

4. The process according to claim 3, wherein the extractant is chosen from the group comprising malonamides, alkyl sulfides, sulfoxides, hydroxyoximes, amines, ammonium salts, alkyl phosphine oxides, phosphine sulfides, ketones, thio and dithio-diglycolamides.

5. The process according to claim 1, wherein:
said second aqueous solution comprises more than 50% of the at least one metal chosen from the platinum group metals and gold comprised in the first organic liquid composition; and/or
said second aqueous solution comprises less than 5% of the diluent comprised in the first organic liquid composition; and/or
said second aqueous solution comprises less than 2% of the extractant comprised in the first organic liquid composition; and/or
said second aqueous solution comprises more than 80% of the surfactant comprised in the first aqueous solution.

6. The process according to claim 1, further comprising, after step b), a step c) of performing a platinum group metal or gold-catalyzed reaction under micellar conditions by contacting said second aqueous solution with the reactants of said platinum group metal or gold-catalyzed reaction to obtain the product of the platinum group metal or gold-catalyzed reaction under micellar conditions.

7. The process according to claim 3, wherein the first organic liquid composition is obtained by extracting an original aqueous phase comprising at least one metal chosen from the platinum group metals and gold, with said extractant in presence of said diluent.

8. The process according to claim 1, wherein said at least one metal chosen from the platinum group metals and gold originates from an aqueous phase comprising nitric acid.

9. The process according to claim 1, wherein the surfactant is selected from:

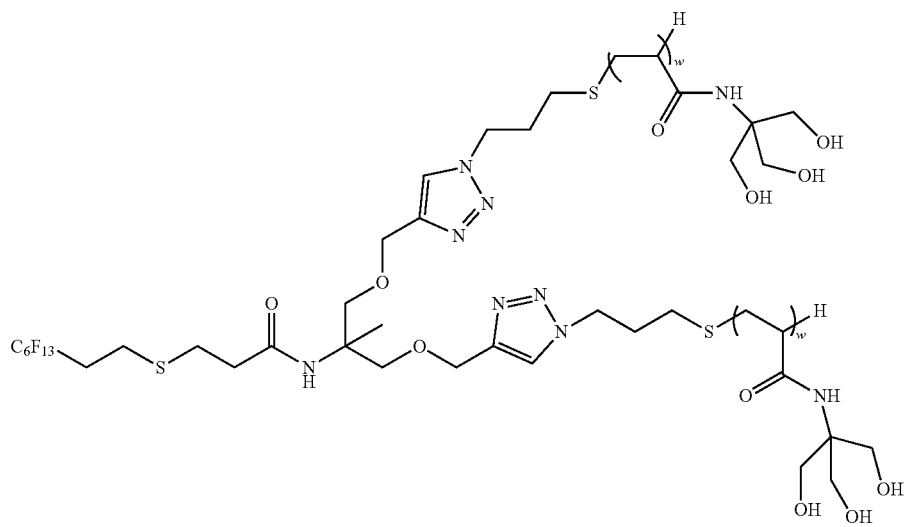

F6 G0diTAC (w*2)

-continued
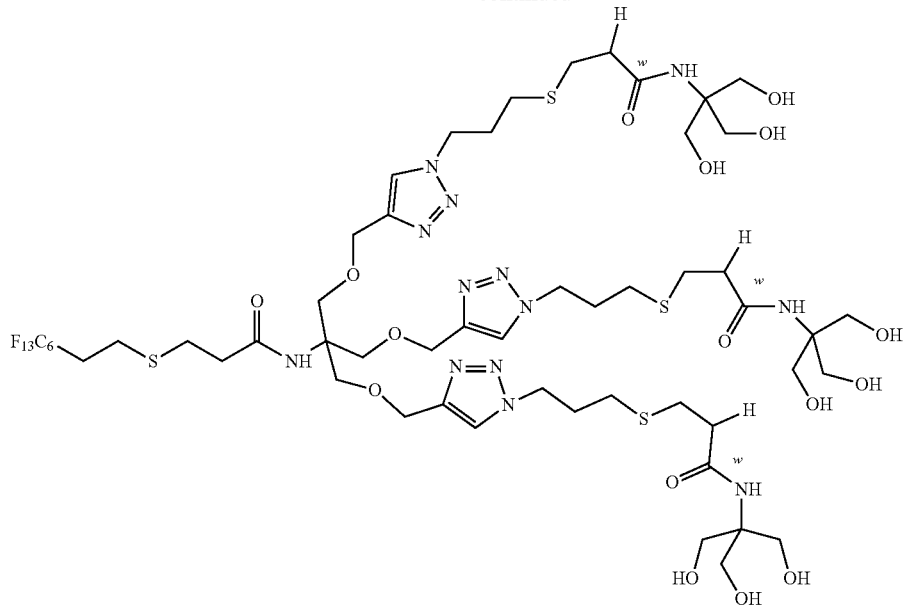
F$_6$G$_0$ triTAC (w*3)
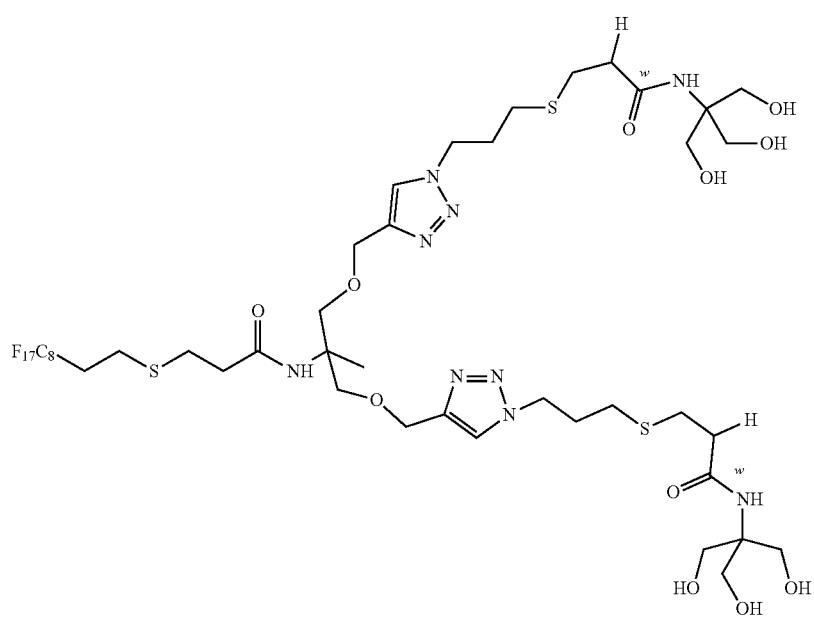
F$_8$G$_0$ diTAC (w*2)

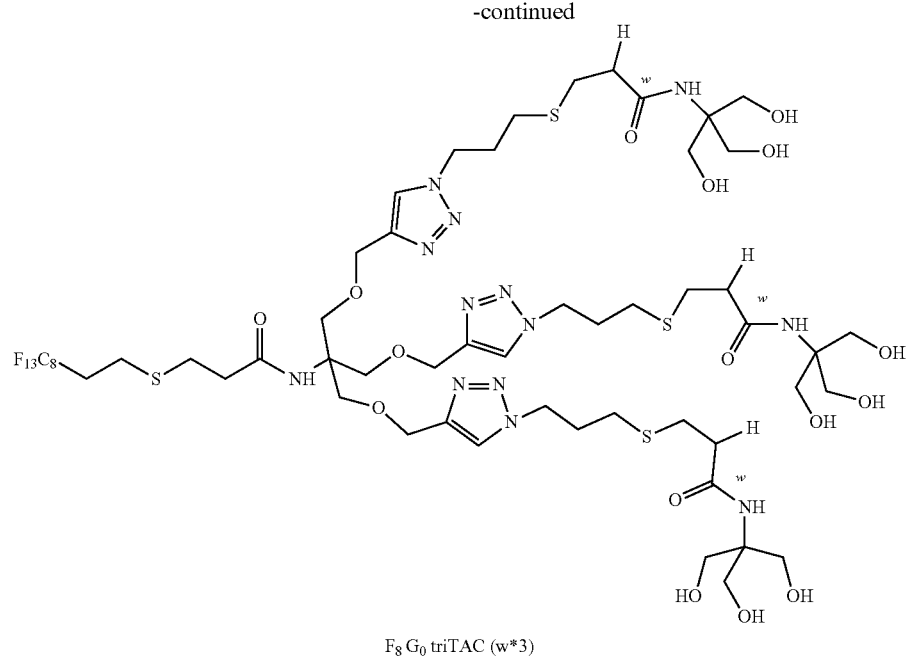
F$_8$G$_0$ triTAC (w*3)
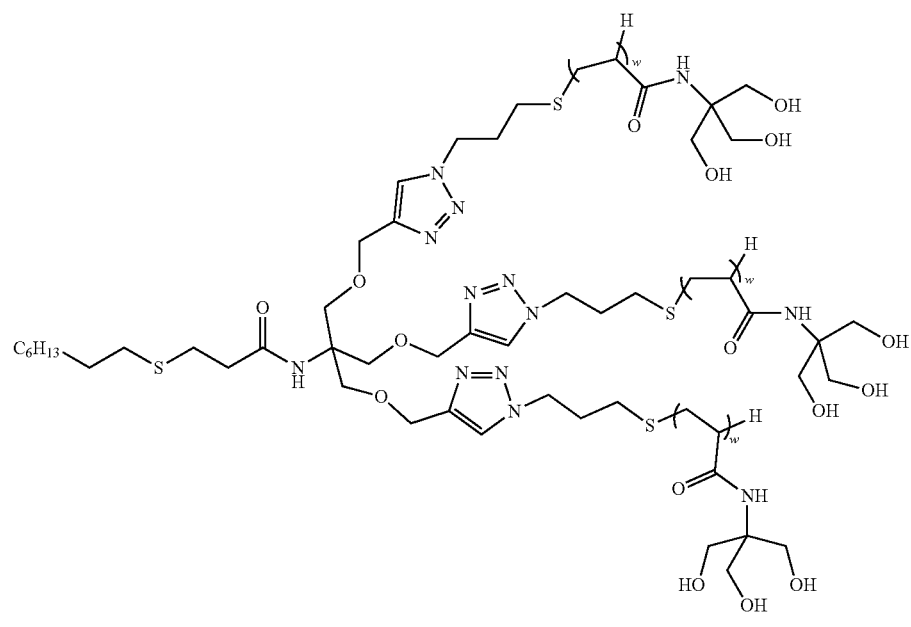
H8G$_0$triTAC

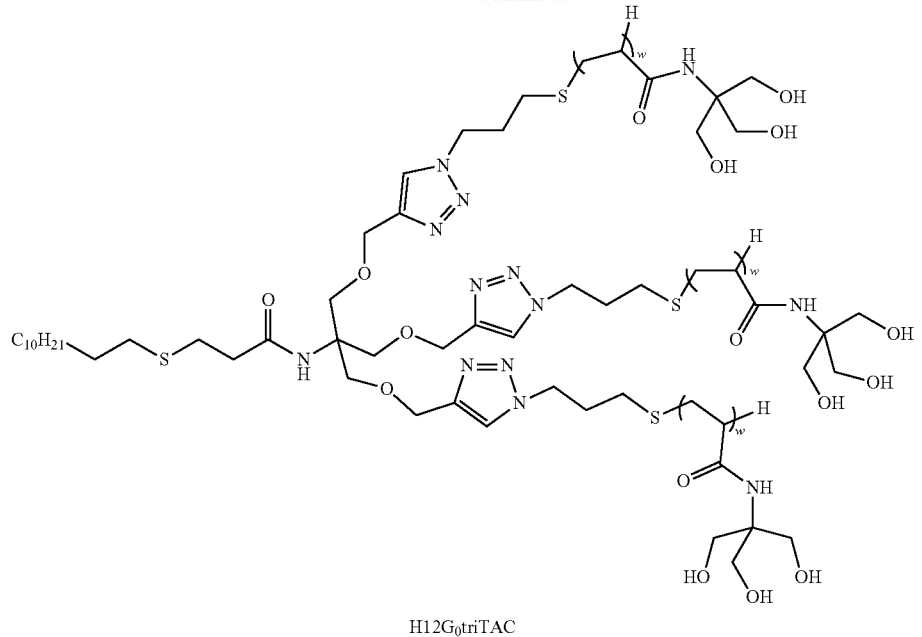
H12G₀triTAC
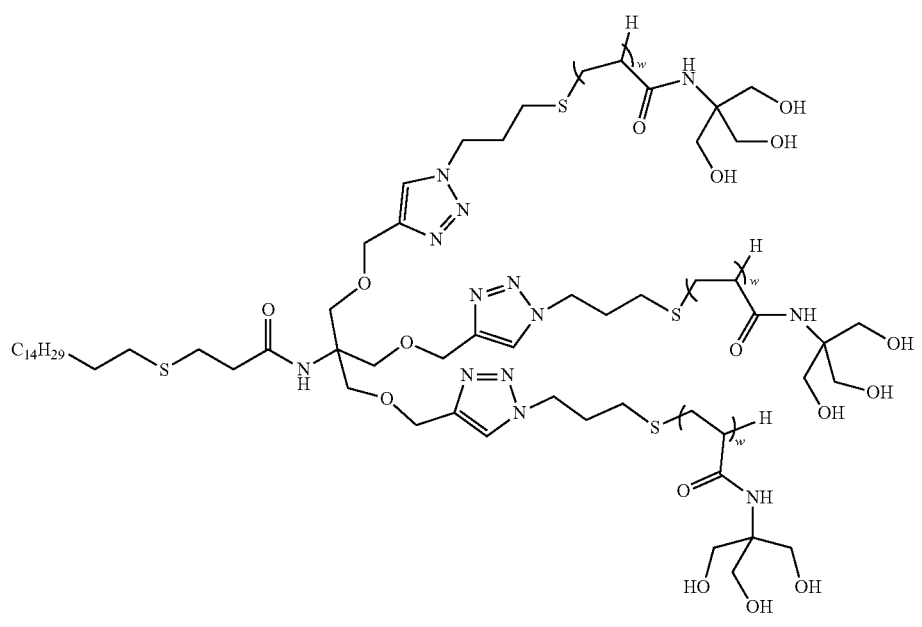
H16G₀triTAC

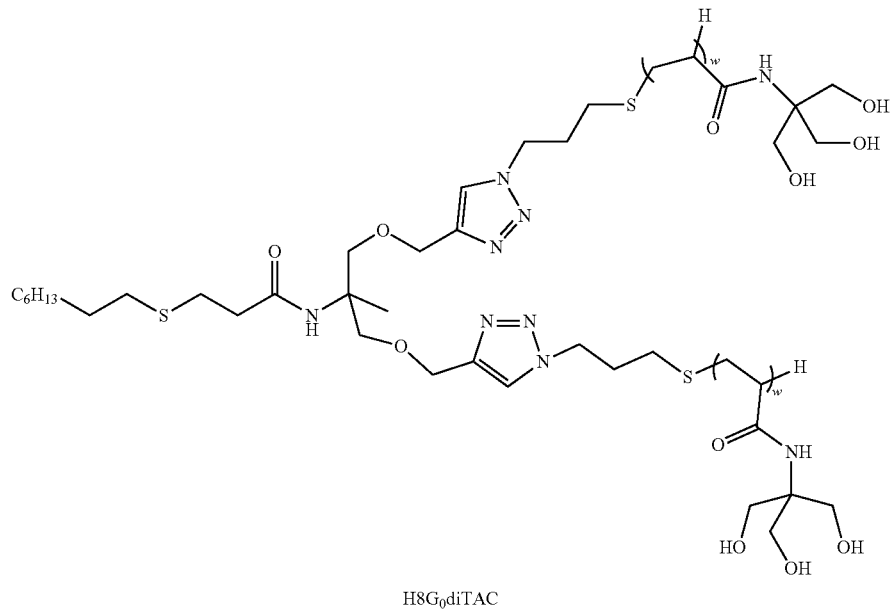
H8G₀diTAC
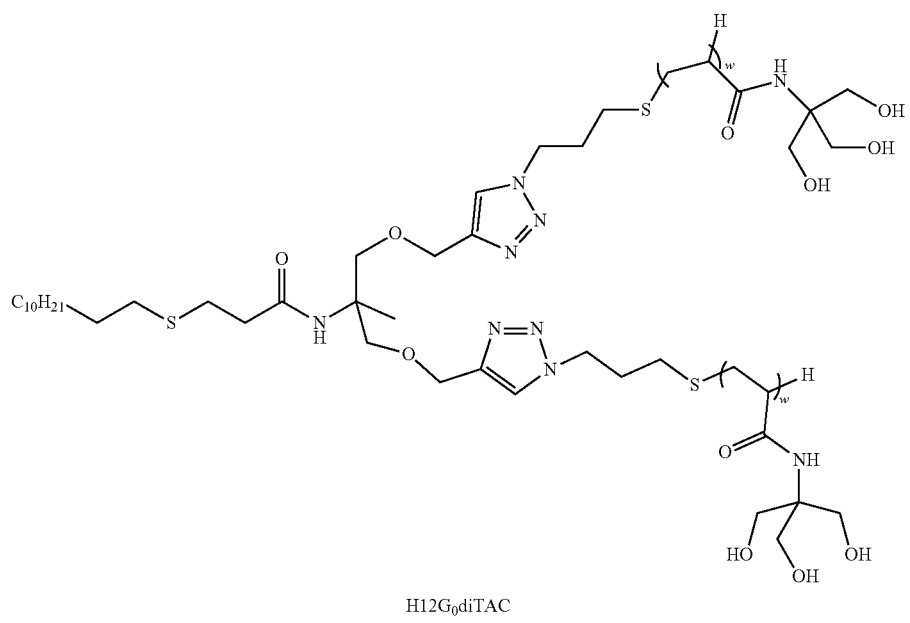
H12G₀diTAC

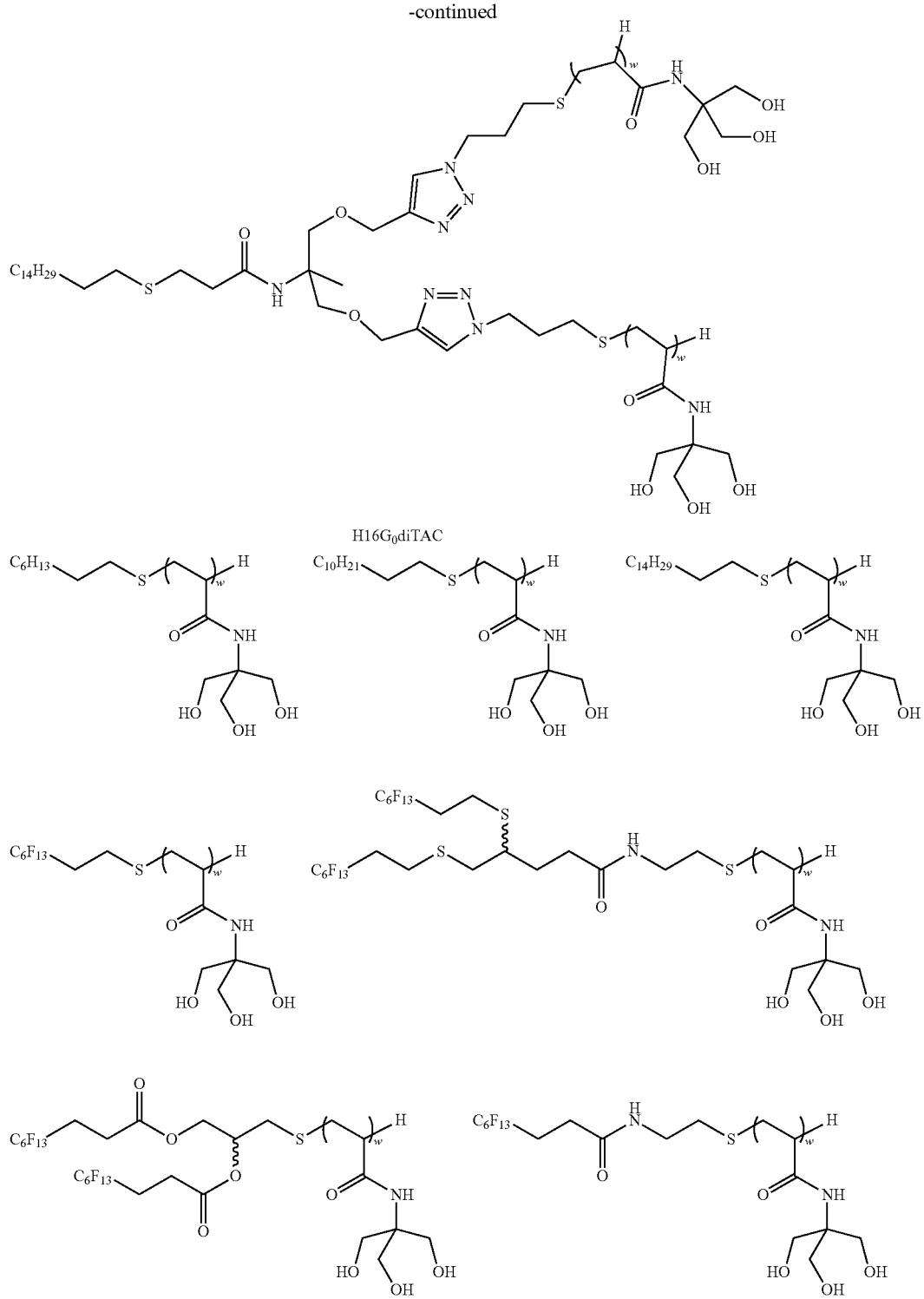

wherein w is as defined in claim 1.

10. The process according to claim 1, wherein the at least one metal chosen from the platinum group metals and gold is palladium.

11. A process of extracting at least one metal chosen from the platinum group metals and gold from a liquid composition to an aqueous solution, said liquid composition comprising:

at least one metal chosen from the platinum group metals and gold, and an organic solvent, said organic solvent being water immiscible, wherein the process further comprises contacting the liquid composition with a surfactant comprising:

a hydrophobic central core of valence m equal to 1, 2 or 3;

when m=1, a hydrophilic group G of the following formula, attached to the central core:

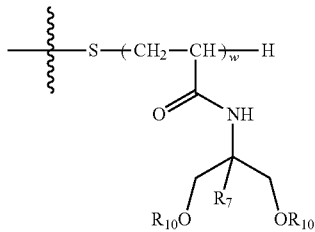

wherein:
$R_7$ is selected from H, $C_1$-$C_6$ alkyl and $CH_2OR_{10}$;
$R_{10}$ is H or a monosaccharide selected from glucose, galactose, mannose;
w is an integer from 1 to 30;
when m=2 or 3, the surfactant being then a dendrimer of generation n,
generation chains attached to the central core and branching around the core; and
an hydrophilic terminal group at the end of each generation chain;
wherein
n is an integer from 0 to 12;
the hydrophilic terminal group comprises:
a mono-, oligo- or polysaccharide residue,
a cyclodextrin residue,
a polyethylene glycol (PEG) residue,
a peptide residue,
a tris(hydroxymethyl)aminoethane (Tris), or
a 2-amino-2-methylpropane-1,3-diol;
the central core being:
when m=1, a -L'-W' group,
wherein:
W' is $R_F$ or a group selected from W'$_1$, W'$_2$ or W'$_3$:

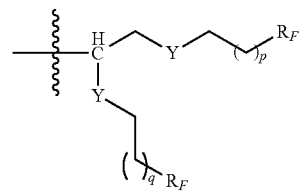

W'$_1$

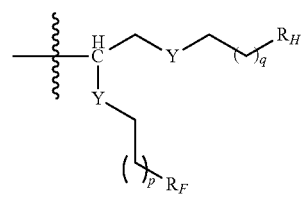

W'$_2$

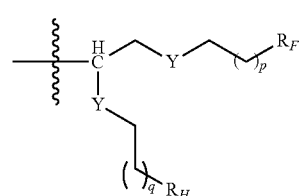

W'$_3$ $R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L' is a linear or branched $C_1$-$C_{12}$ alkylene group, optionally interrupted by one or more groups Y';
Y' at each occurrence is chosen from —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH—, —O— or Y at each occurrence is chosen from —S—, —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH— or —O—;

when m=2 or 3, a group of formula (Ia) or (Ib):

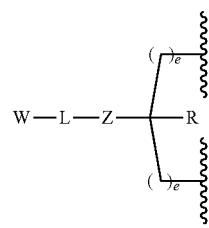

(Ia)

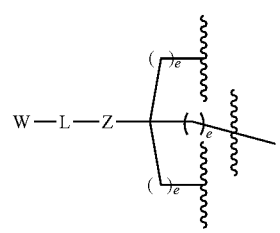

(Ib)

wherein:
W is $R_F$ or a group selected from $W_0$, $W_1$, $W_2$ or $W_3$:

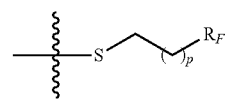

$W_0$

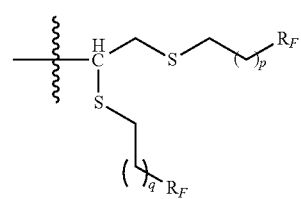

$W_1$

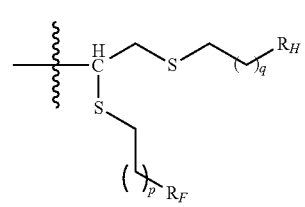

$W_2$

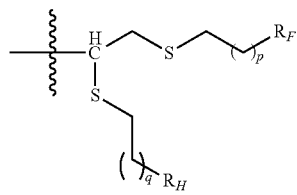
W₃

$R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L is a linear or branched $C_1$-$C_{12}$ alkylene group, optionally interrupted by one or more —O—, —S—,
Z is C(=O)NH or NHC(=O),
R is a $C_1$-$C_6$ alkyl group, and
e is at each occurrence independently selected from 0, 1, 2, 3 or 4.

12. A micelle or an aqueous solution comprising at least one metal chosen from the platinum group metals and gold and a surfactant as comprising:
- a hydrophobic central core of valence m equal to 1, 2 or 3;
- when m=1, a hydrophilic group G of the following formula, attached to the central core:

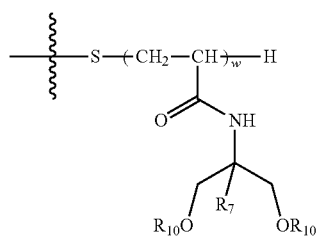

wherein:
$R_7$ is selected from H, $C_1$-$C_6$ alkyl and $CH_2OR_{10}$;
$R_{10}$ is H or a monosaccharide selected from glucose, galactose, mannose;
w is an integer from 1 to 30;
- when m=2 or 3, the surfactant being then a dendrimer of generation n,
  - generation chains attached to the central core and branching around the core; and
  - an hydrophilic terminal group at the end of each generation chain;
wherein
n is an integer from 0 to 12;
the hydrophilic terminal group comprises:
- a mono-, oligo- or polysaccharide residue,
- a cyclodextrin residue,
- a polyethylene glycol (PEG) residue,
- a peptide residue,
- a tris(hydroxymethyl)aminoethane (Tris), or
- a 2-amino-2-methylpropane-1,3-diol;
the central core being:
when m=1, a -L'-W' group,
wherein:
W' is $R_F$ or a group selected from W'₁, W'₂ or W'₃:

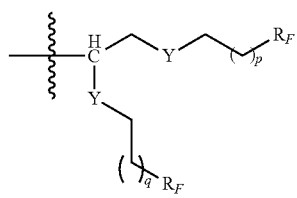
W'₁

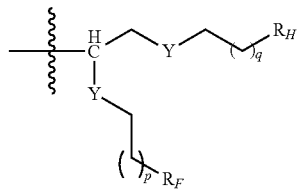
W'₂

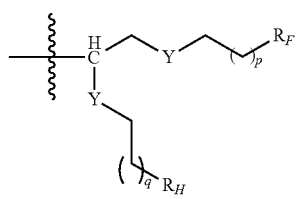
W'₃

$R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L' is a linear or branched $C_1$-$C_{12}$ alkylene group, optionally interrupted by one or more groups Y';
Y' at each occurrence is chosen from —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH—, —O— or Y at each occurrence is chosen from —S—, —OC(=O)—, —C(=O)O—, —O—C(=O)—NH—, —NH—C(=O)—O—, —OC(=O)—O—, —NHC(=O)—, —C(=O)—NH, —NHC(=O)NH—, —NHC(=O)O—, —O—C(=O)—NH—, —NH— or —O—;
when m=2 or 3, a group of formula (Ia) or (Ib):

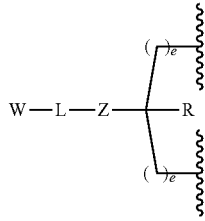
(Ia)

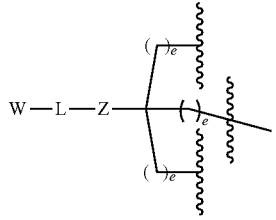
(Ib)

wherein:
W is $R_F$ or a group selected from $W_0$, $W_1$, $W_2$ or $W_3$:

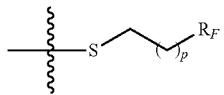
$W_0$

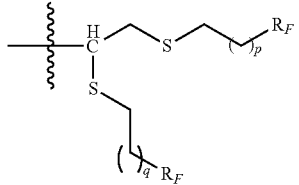
$W_1$

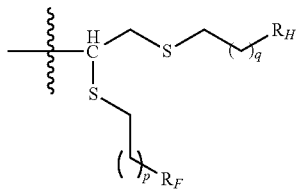
$W_2$

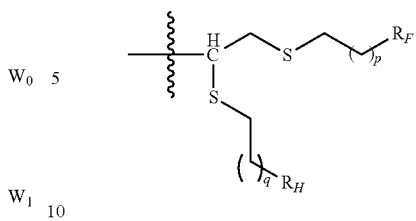
$W_3$ $R_F$ is a $C_4$-$C_{10}$ perfluoroalkyl or a $C_1$-$C_{24}$ alkyl group,
$R_H$ is a $C_1$-$C_{24}$ alkyl group,
p is 0, 1, 2, 3 or 4;
q is 0, 1, 2, 3 or 4;
L is a linear or branched $C_1$-$C_{12}$ alkylene group, optionally interrupted by one or more —O—, —S—,
Z is C(=O)NH or NHC(=O),
R is a $C_1$-$C_6$ alkyl group, and
e is at each occurrence independently selected from 0, 1, 2, 3 or 4.

13. A platinum group metal or gold-catalyzed reaction process under micellar conditions comprising the micelle or aqueous solution according to claim 12.

* * * * *